(12) United States Patent
Vacca et al.

(10) Patent No.: US 12,071,426 B2
(45) Date of Patent: Aug. 27, 2024

(54) IRE1 SMALL MOLECULE INHIBITORS

(71) Applicant: Cornell University, Ithaca, NY (US)

(72) Inventors: Joseph P. Vacca, Telford, PA (US); Sarah Elizabeth Bettigole, New York, NY (US)

(73) Assignee: Cornell University, Ithaca, NY (US)

( * ) Notice: Subject to any disclaimer, the term of this patent is extended or adjusted under 35 U.S.C. 154(b) by 491 days.

(21) Appl. No.: 17/299,684

(22) PCT Filed: Dec. 2, 2019

(86) PCT No.: PCT/US2019/063921
§ 371 (c)(1),
(2) Date: Jun. 3, 2021

(87) PCT Pub. No.: WO2020/117635
PCT Pub. Date: Jun. 11, 2020

(65) Prior Publication Data
US 2022/0356168 A1    Nov. 10, 2022

Related U.S. Application Data

(60) Provisional application No. 62/774,794, filed on Dec. 3, 2018.

(51) Int. Cl.
*C07D 401/14*    (2006.01)
*C07D 471/04*    (2006.01)

(52) U.S. Cl.
CPC ......... *C07D 401/14* (2013.01); *C07D 471/04* (2013.01)

(58) Field of Classification Search
CPC .......................... C07D 401/14; C07D 471/04
USPC .................................................. 514/264.11
See application file for complete search history.

(56) References Cited

U.S. PATENT DOCUMENTS

| 2012/0238587 A1 | 9/2012 | Lee et al. |
| 2018/0265497 A1 | 9/2018 | Braun et al. |

FOREIGN PATENT DOCUMENTS

| CN | 108239074 A | 7/2018 |
| JP | 2022511477 | 1/2022 |
| WO | WO-2018102751 A1 | 6/2018 |
| WO | 2018166528 | 9/2018 |
| WO | WO-2018222918 A1 | 12/2018 |
| WO | WO-2019094641 A1 | 5/2019 |
| WO | WO-2020117635 A1 | 6/2020 |

OTHER PUBLICATIONS

"International Application Serial No. PCT/US2019/063921, International Preliminary Report on Patentability mailed Jun. 17, 2021", 9 pgs.
"International Application Serial No. PCT/US2019/063921, International Search Report mailed Feb. 20, 2020", 7 pgs.
"International Application Serial No. PCT/US2019/063921, Written Opinion mailed Feb. 20, 2020", 7 pgs.
Morita, Shuhei, et al., "Targeting ABL-IRE1a signaling spares ER-stressed pancreatic ß-cells to reverse autoimmune diabetes", Cell Metabolism, Cell Press, United States, vol. 25, No. 4, (Apr. 4, 2017), 883.
"European Application Serial No. 19828388.9, Communication Pursuant to Article 94(3) EPC mailed Jun. 30, 2022", 5 pgs.
"European Application Serial No. 19828388.9, Response filed Sep. 20, 2022 to Communication Pursuant to Article 94(3) EPC mailed Jun. 30, 2022", 13 pgs.
"Canadian Application Serial No. 3,121,755, Examiner's Rule 86(2) Requisition mailed Oct. 21, 2022, 3 pgs", 3 pgs.
"European Application Serial No. 19828388.9, Communication Pursuant to Article 94(3) EPC mailed Apr. 3, 2023", 4 pgs.
"European Application Serial No. 19828388.9, Response Filed Jul. 3, 2023 to Communication Pursuant to Article 94(3) EPC mailed Apr. 3, 2023", 12 pgs.
"Japanese Application Serial No. 2021-531523, Notification of Reasons for Refusal mailed Nov. 28, 2023", w English Translation, 4 pgs.

*Primary Examiner* — Kristin A Vajda
(74) *Attorney, Agent, or Firm* — Schwegman Lundberg & Woessner, P.A.

(57) ABSTRACT

Provided herein are small molecule inhibitors for the targeting or IRE1 protein family members. Binding may be direct or indirect. Further provided herein are methods of using IRE1 small molecule inhibitors for use in treating or ameliorating cancer in a subject. Moreover, IRE1 small molecule inhibitors described herein are for the treatment of cancer, where the cancer is a solid or hematologic cancer.

23 Claims, 2 Drawing Sheets
Specification includes a Sequence Listing.

SEQUENCE LISTING

<160> NUMBER OF SEQ ID NOS: 7

<210> SEQ ID NO 1
<211> LENGTH: 977
<212> TYPE: PRT
<213> ORGANISM: Homo sapiens

<400> SEQUENCE: 1

Met Pro Ala Arg Arg Leu Leu Leu Leu Leu Thr Leu Leu Leu Pro Gly
1               5                   10                  15

Leu Gly Ile Phe Gly Ser Thr Ser Thr Val Thr Leu Pro Glu Thr Leu
            20                  25                  30

Leu Phe Val Ser Thr Leu Asp Gly Ser Leu His Ala Val Ser Lys Arg
        35                  40                  45

Thr Gly Ser Ile Lys Trp Thr Leu Lys Glu Asp Pro Val Leu Gln Val
    50                  55                  60

Pro Thr His Val Glu Glu Pro Ala Phe Leu Pro Asp Pro Asn Asp Gly
65                  70                  75                  80

Ser Leu Tyr Thr Leu Gly Ser Lys Asn Asn Glu Gly Leu Thr Lys Leu
                85                  90                  95

```
Pro Phe Thr Ile Pro Glu Leu Val Gln Ala Ser Pro Cys Arg Ser Ser
                100                 105                 110

Asp Gly Ile Leu Tyr Met Gly Lys Lys Gln Asp Ile Trp Tyr Val Ile
            115                 120                 125

Asp Leu Leu Thr Gly Glu Lys Gln Gln Thr Leu Ser Ser Ala Phe Ala
        130                 135                 140

Asp Ser Leu Cys Pro Ser Thr Ser Leu Leu Tyr Leu Gly Arg Thr Glu
145                 150                 155                 160

Tyr Thr Ile Thr Met Tyr Asp Thr Lys Thr Arg Glu Leu Arg Trp Asn
                165                 170                 175

Ala Thr Tyr Phe Asp Tyr Ala Ala Ser Leu Pro Glu Asp Asp Val Asp
            180                 185                 190

Tyr Lys Met Ser His Phe Val Ser Asn Gly Asp Gly Leu Val Val Thr
        195                 200                 205

Val Asp Ser Glu Ser Gly Asp Val Leu Trp Ile Gln Asn Tyr Ala Ser
210                 215                 220

Pro Val Val Ala Phe Tyr Val Trp Gln Arg Glu Gly Leu Arg Lys Val
225                 230                 235                 240

Met His Ile Asn Val Ala Val Glu Thr Leu Arg Tyr Leu Thr Phe Met
                245                 250                 255

Ser Gly Glu Val Gly Arg Ile Thr Lys Trp Lys Tyr Pro Phe Pro Lys
            260                 265                 270

Glu Thr Glu Ala Lys Ser Lys Leu Thr Pro Thr Leu Tyr Val Gly Lys
        275                 280                 285

Tyr Ser Thr Ser Leu Tyr Ala Ser Pro Ser Met Val His Glu Gly Val
290                 295                 300

Ala Val Val Pro Arg Gly Ser Thr Leu Pro Leu Leu Glu Gly Pro Gln
305                 310                 315                 320

Thr Asp Gly Val Thr Ile Gly Asp Lys Gly Glu Cys Val Ile Thr Pro
                325                 330                 335

Ser Thr Asp Val Lys Phe Asp Pro Gly Leu Lys Ser Lys Asn Lys Leu
            340                 345                 350

Asn Tyr Leu Arg Asn Tyr Trp Leu Leu Ile Gly His His Glu Thr Pro
        355                 360                 365

Leu Ser Ala Ser Thr Lys Met Leu Glu Arg Phe Pro Asn Asn Leu Pro
370                 375                 380

Lys His Arg Glu Asn Val Ile Pro Ala Asp Ser Glu Lys Lys Ser Phe
385                 390                 395                 400

Glu Glu Val Ile Asn Leu Val Asp Gln Thr Ser Glu Asn Ala Pro Thr
                405                 410                 415

Thr Val Ser Arg Asp Val Glu Glu Lys Pro Ala His Ala Pro Ala Arg
            420                 425                 430

Pro Glu Ala Pro Val Asp Ser Met Leu Lys Asp Met Ala Thr Ile Ile
        435                 440                 445

Leu Ser Thr Phe Leu Leu Ile Gly Trp Val Ala Phe Ile Ile Thr Tyr
450                 455                 460

Pro Leu Ser Met His Gln Gln Gln Leu Gln His Gln Gln Phe Gln
465                 470                 475                 480

Lys Glu Leu Glu Lys Ile Gln Leu Leu Gln Gln Gln Gln Gln Leu
                485                 490                 495

Pro Phe His Pro Pro Gly Asp Thr Ala Gln Asp Gly Glu Leu Leu Asp
            500                 505                 510

Thr Ser Gly Pro Tyr Ser Glu Ser Ser Gly Thr Ser Ser Pro Ser Thr
```

```
              515                 520                 525
Ser Pro Arg Ala Ser Asn His Ser Leu Cys Ser Gly Ser Ala Ser
            530                 535                 540
Lys Ala Gly Ser Ser Pro Ser Leu Glu Gln Asp Asp Gly Asp Glu Glu
545                 550                 555                 560
Thr Ser Val Val Ile Val Gly Lys Ile Ser Phe Cys Pro Lys Asp Val
                565                 570                 575
Leu Gly His Gly Ala Glu Gly Thr Ile Val Tyr Arg Gly Met Phe Asp
            580                 585                 590
Asn Arg Asp Val Ala Val Lys Arg Ile Leu Pro Glu Cys Phe Ser Phe
            595                 600                 605
Ala Asp Arg Glu Val Gln Leu Leu Arg Glu Ser Asp Glu His Pro Asn
            610                 615                 620
Val Ile Arg Tyr Phe Cys Thr Glu Lys Asp Arg Gln Phe Gln Tyr Ile
625                 630                 635                 640
Ala Ile Glu Leu Cys Ala Ala Thr Leu Gln Glu Tyr Val Glu Gln Lys
                645                 650                 655
Asp Phe Ala His Leu Gly Leu Glu Pro Ile Thr Leu Leu Gln Gln Thr
            660                 665                 670
Thr Ser Gly Leu Ala His Leu His Ser Leu Asn Ile Val His Arg Asp
            675                 680                 685
Leu Lys Pro His Asn Ile Leu Ile Ser Met Pro Asn Ala His Gly Lys
            690                 695                 700
Ile Lys Ala Met Ile Ser Asp Phe Gly Leu Cys Lys Lys Leu Ala Val
705                 710                 715                 720
Gly Arg His Ser Phe Ser Arg Arg Ser Gly Val Pro Gly Thr Glu Gly
                725                 730                 735
Trp Ile Ala Pro Glu Met Leu Ser Glu Asp Cys Lys Glu Asn Pro Thr
            740                 745                 750
Tyr Thr Val Asp Ile Phe Ser Ala Gly Cys Val Phe Tyr Tyr Val Ile
            755                 760                 765
Ser Glu Gly Ser His Pro Phe Gly Lys Ser Leu Gln Arg Gln Ala Asn
            770                 775                 780
Ile Leu Leu Gly Ala Cys Ser Leu Asp Cys Leu His Pro Glu Lys His
785                 790                 795                 800
Glu Asp Val Ile Ala Arg Glu Leu Ile Glu Lys Met Ile Ala Met Asp
                805                 810                 815
Pro Gln Lys Arg Pro Ser Ala Lys His Val Leu Lys His Pro Phe Phe
            820                 825                 830
Trp Ser Leu Glu Lys Gln Leu Gln Phe Phe Gln Asp Val Ser Asp Arg
            835                 840                 845
Ile Glu Lys Glu Ser Leu Asp Gly Pro Ile Val Lys Gln Leu Glu Arg
            850                 855                 860
Gly Gly Arg Ala Val Val Lys Met Asp Trp Arg Glu Asn Ile Thr Val
865                 870                 875                 880
Pro Leu Gln Thr Asp Leu Arg Lys Phe Arg Thr Tyr Lys Gly Gly Ser
                885                 890                 895
Val Arg Asp Leu Leu Arg Ala Met Arg Asn Lys Lys His His Tyr Arg
            900                 905                 910
Glu Leu Pro Ala Glu Val Arg Glu Thr Leu Gly Ser Leu Pro Asp Asp
            915                 920                 925
Phe Val Cys Tyr Phe Thr Ser Arg Phe Pro His Leu Leu Ala His Thr
            930                 935                 940
```

```
Tyr Arg Ala Met Glu Leu Cys Ser His Glu Arg Leu Phe Gln Pro Tyr
945                 950                 955                 960

Tyr Phe His Glu Pro Pro Glu Pro Gln Pro Val Thr Pro Asp Ala
                965                 970                 975

Leu

<210> SEQ ID NO 2
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 2
cauguccgca gcacaug                                                      17

<210> SEQ ID NO 3
<211> LENGTH: 17
<212> TYPE: RNA
<213> ORGANISM: Artificial Sequence
<220> FEATURE:
<223> OTHER INFORMATION: Description of Artificial Sequence: Synthetic
      probe

<400> SEQUENCE: 3
caugucccca gcacaug                                                      17

<210> SEQ ID NO 4
<211> LENGTH: 434
<212> TYPE: PRT
<213> ORGANISM: Saccharomyces cerevisiae

<400> SEQUENCE: 4

Ser Arg Ile Ala Asn Ile Pro Asn Phe Glu Gln Ser Leu Lys Asn Leu
1               5                   10                  15

Val Val Ser Glu Lys Ile Leu Gly Tyr Gly Ser Ser Gly Thr Val Val
                20                  25                  30

Phe Gln Gly Ser Phe Gln Gly Arg Pro Val Ala Val Lys Arg Met Leu
            35                  40                  45

Ile Asp Phe Cys Asp Ile Ala Leu Met Glu Ile Lys Leu Leu Thr Glu
        50                  55                  60

Ser Asp His Pro Asn Val Ile Arg Tyr Tyr Cys Ser Glu Thr Thr
65                  70                  75                  80

Asp Arg Phe Leu Tyr Ile Ala Leu Glu Leu Cys Asn Leu Asn Leu Gln
                85                  90                  95

Asp Leu Val Glu Ser Lys Asn Val Ser Asp Glu Asn Leu Lys Leu Gln
            100                 105                 110

Lys Glu Tyr Asn Pro Ile Ser Leu Leu Arg Gln Ile Ala Ser Gly Val
        115                 120                 125

Ala His Leu His Ser Leu Lys Ile Ile His Arg Asp Leu Lys Pro Gln
    130                 135                 140

Asn Ile Leu Val Ser Thr Ser Ser Arg Phe Thr Ala Asp Gln Gln Thr
145                 150                 155                 160

Gly Ala Glu Asn Leu Arg Ile Leu Ile Ser Asp Phe Gly Leu Cys Lys
                165                 170                 175

Lys Leu Asp Ser Gly Gln Ser Ser Phe Arg Thr Asn Leu Asn Asn Pro
            180                 185                 190
```

```
Ser Gly Thr Ser Gly Trp Arg Ala Pro Glu Leu Leu Glu Ser Asn
            195                 200                 205

Asn Leu Gln Thr Lys Arg Arg Leu Thr Arg Ser Ile Asp Ile Phe Ser
    210                 215                 220

Met Gly Cys Val Phe Tyr Tyr Ile Leu Ser Lys Gly Lys His Pro Phe
225                 230                 235                 240

Gly Asp Lys Tyr Ser Arg Glu Ser Asn Ile Ile Arg Gly Ile Phe Ser
                245                 250                 255

Leu Asp Glu Met Lys Cys Leu His Asp Arg Ser Leu Ile Ala Glu Ala
                260                 265                 270

Thr Asp Leu Ile Ser Gln Met Ile Asp His Asp Pro Leu Lys Arg Pro
                275                 280                 285

Thr Ala Met Lys Val Leu Arg His Pro Leu Phe Trp Pro Lys Ser Lys
                290                 295                 300

Lys Leu Glu Phe Leu Leu Lys Val Ser Asp Arg Leu Glu Ile Glu Asn
305                 310                 315                 320

Arg Asp Pro Pro Ser Ala Leu Leu Met Lys Phe Asp Ala Gly Ser Asp
                325                 330                 335

Phe Val Ile Pro Ser Gly Asp Trp Thr Val Lys Phe Asp Lys Ile Phe
                340                 345                 350

Met Asp Asn Leu Glu Arg Tyr Arg Lys Tyr His Ser Ser Lys Leu Met
                355                 360                 365

Asp Leu Leu Arg Ala Leu Arg Asn Lys Tyr His His Phe Met Asp Leu
                370                 375                 380

Pro Glu Asp Ile Ala Glu Leu Met Gly Pro Val Pro Asp Gly Phe Tyr
385                 390                 395                 400

Asp Tyr Phe Ile Lys Arg Phe Pro Asn Leu Leu Ile Gly Val Tyr Met
                405                 410                 415

Ile Val Lys Glu Asn Leu Ser Asp Asp Gln Ile Leu Arg Glu Phe Leu
                420                 425                 430

Tyr Ser

<210> SEQ ID NO 5
<211> LENGTH: 424
<212> TYPE: PRT
<213> ORGANISM: Homo sapiens

<400> SEQUENCE: 5

Asp Asp Gly Asp Glu Glu Thr Ser Val Val Ile Val Gly Lys Ile Ser
1               5                   10                  15

Phe Cys Pro Lys Asp Val Leu Gly His Gly Ala Glu Gly Thr Ile Val
                20                  25                  30

Tyr Arg Gly Met Phe Asp Asn Arg Asp Val Ala Val Lys Arg Ile Leu
            35                  40                  45

Pro Glu Cys Phe Ser Phe Ala Asp Arg Glu Val Gln Leu Leu Arg Glu
50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln
                85                  90                  95

Glu Tyr Val Glu Gln Lys Asp Cys Phe Ala His Leu Gly Leu Glu Pro
            100                 105                 110

Ile Thr Leu Leu Gln Gln Thr Thr Ser Gly Leu Ala His Leu His Ser
            115                 120                 125
```

-continued

Leu Asn Ile Val His Arg Asp Leu Lys Pro His Asn Ile Leu Ile Ser
130                 135                 140

Met Pro Asn Ala His Gly Lys Ile Lys Ala Met Ile Ser Asp Phe Gly
145                 150                 155                 160

Leu Cys Lys Lys Leu Ala Val Gly Arg His Ser Phe Ser Arg Arg Ser
                165                 170                 175

Gly Val Pro Gly Thr Glu Gly Trp Ile Ala Pro Glu Met Leu Ser Glu
            180                 185                 190

Asp Cys Lys Glu Asn Pro Thr Tyr Thr Val Asp Ile Phe Ser Ala Gly
        195                 200                 205

Cys Val Phe Tyr Tyr Val Val Ser Glu Gly Ser His Pro Phe Gly Lys
210                 215                 220

Ser Leu Gln Arg Gln Ala Asn Ile Leu Leu Gly Ala Cys Ser Leu Asp
225                 230                 235                 240

Cys Leu His Pro Glu Lys His Glu Asp Val Ile Ala Arg Glu Leu Ile
                245                 250                 255

Glu Lys Met Ile Ala Met Asp Pro Gln Lys Arg Pro Ser Ala Asn Asp
            260                 265                 270

Val Leu Lys His Pro Phe Phe Trp Ser Leu Glu Lys Gln Leu Gln Phe
        275                 280                 285

Phe Gln Asp Val Ser Asp Arg Ile Glu Lys Glu Ser Leu Asp Gly Pro
290                 295                 300

Ile Val Lys Gln Leu Glu Arg Gly Gly Arg Ala Val Val Lys Met Asp
305                 310                 315                 320

Trp Arg Glu Asn Ile Thr Asp Pro Leu Gln Thr Asp Leu Arg Lys Phe
                325                 330                 335

Arg Thr Tyr Lys Gly Gly Ser Val Arg Asp Leu Leu Arg Ala Met Arg
            340                 345                 350

Asn Lys Lys His His Tyr Arg Asp Leu Pro Glu Glu Val Arg Glu Thr
        355                 360                 365

Leu Gly Thr Leu Pro Asp Asp Phe Val Cys Tyr Phe Thr Ser Arg Phe
370                 375                 380

Pro His Leu Leu Ala His Thr Tyr Arg Ala Met Glu Leu Cys Ser His
385                 390                 395                 400

Glu Arg Leu Phe Gln Pro Tyr Tyr Phe His Glu Pro Glu Pro Gln
                405                 410                 415

Pro Pro Val Thr Pro Asp Ala Leu
            420

<210> SEQ ID NO 6
<211> LENGTH: 423
<212> TYPE: PRT
<213> ORGANISM: Mus musculus

<400> SEQUENCE: 6

Asp Asp Glu Asp Glu Glu Thr Arg Met Val Ile Val Gly Lys Ile Ser
1               5                   10                  15

Phe Cys Pro Lys Asp Val Leu Gly His Gly Ala Glu Gly Thr Ile Val
                20                  25                  30

Tyr Lys Gly Met Phe Asp Asn Arg Asp Val Ala Val Lys Arg Ile Leu
            35                  40                  45

Pro Glu Cys Phe Ser Phe Ala Asp Arg Glu Val Gln Leu Leu Arg Glu
        50                  55                  60

Ser Asp Glu His Pro Asn Val Ile Arg Tyr Phe Cys Thr Glu Lys Asp
65                  70                  75                  80

```
Arg Gln Phe Gln Tyr Ile Ala Ile Glu Leu Cys Ala Ala Thr Leu Gln
                85                  90                  95

Glu Tyr Val Glu Gln Lys Asp Phe Ala His Leu Gly Leu Glu Pro Ile
            100                 105                 110

Thr Leu Leu His Gln Thr Thr Ser Gly Leu Ala His Leu His Ser Leu
        115                 120                 125

Asn Ile Val His Arg Asp Leu Lys Pro His Asn Ile Leu Leu Ser Met
130                 135                 140

Pro Asn Ala His Gly Arg Ile Lys Ala Met Ile Ser Asp Phe Gly Leu
145                 150                 155                 160

Cys Lys Lys Leu Ala Val Gly Arg His Ser Phe Ser Arg Arg Ser Gly
                165                 170                 175

Val Pro Gly Thr Glu Gly Trp Ile Ala Pro Glu Met Leu Ser Glu Asp
            180                 185                 190

Cys Lys Asp Asn Pro Thr Tyr Thr Val Asp Ile Phe Ser Ala Gly Cys
        195                 200                 205

Val Phe Tyr Tyr Val Ile Ser Glu Gly Asn His Pro Phe Gly Lys Ser
210                 215                 220

Leu Gln Arg Gln Ala Asn Ile Leu Leu Gly Ala Cys Asn Leu Asp Cys
225                 230                 235                 240

Phe His Ser Asp Lys His Glu Asp Val Ile Ala Arg Glu Leu Ile Glu
                245                 250                 255

Lys Met Ile Ala Met Asp Pro Gln Gln Arg Pro Ser Ala Lys His Val
            260                 265                 270

Leu Lys His Pro Phe Phe Trp Ser Leu Glu Lys Gln Leu Gln Phe Phe
        275                 280                 285

Gln Asp Val Ser Asp Arg Ile Glu Lys Glu Ala Leu Asp Gly Pro Ile
290                 295                 300

Val Arg Gln Leu Glu Arg Gly Arg Ala Val Val Lys Met Asp Trp
305                 310                 315                 320

Arg Glu Asn Ile Thr Val Pro Leu Gln Thr Asp Leu Arg Lys Phe Arg
                325                 330                 335

Thr Tyr Lys Gly Gly Ser Val Arg Asp Leu Leu Arg Ala Met Arg Asn
            340                 345                 350

Lys Lys His His Tyr Arg Glu Leu Pro Ala Glu Val Gln Glu Thr Leu
        355                 360                 365

Gly Ser Ile Pro Asp Asp Phe Val Arg Tyr Phe Thr Ser Arg Phe Pro
370                 375                 380

His Leu Leu Ser His Thr Tyr Gln Ala Met Glu Leu Cys Arg His Glu
385                 390                 395                 400

Arg Leu Phe Gln Thr Tyr Tyr Trp His Glu Pro Thr Glu Pro Gln Pro
                405                 410                 415

Pro Val Ile Pro Tyr Ala Leu
            420

<210> SEQ ID NO 7
<211> LENGTH: 423
<212> TYPE: PRT
<213> ORGANISM: Rattus norvegicus

<400> SEQUENCE: 7

Asp Asp Glu Asp Glu Glu Thr Arg Met Val Ile Val Gly Lys Ile Ser
1               5                   10                  15

Phe Cys Pro Lys Asp Val Leu Gly His Gly Ala Glu Gly Thr Ile Val
```

```
                    20                  25                  30
Tyr Lys Gly Met Phe Asp Asn Arg Asp Val Ala Val Lys Arg Ile Leu
            35                  40                  45

Pro Glu Cys Phe Ser Phe Ala Asp Arg Glu Val Gln Leu Leu Arg Glu
        50                  55                  60

Ser Asp Glu His Pro Asn Val Ile Arg Tyr Phe Cys Thr Glu Lys Asp
65                  70                  75                  80

Arg Gln Phe Gln Tyr Ile Ala Ile Glu Leu Cys Ala Ala Thr Leu Gln
                85                  90                  95

Glu Tyr Val Glu Gln Lys Asp Phe Ala His Leu Gly Leu Glu Pro Ile
            100                 105                 110

Thr Leu Leu His Gln Thr Thr Ser Gly Leu Ala His Leu His Ser Leu
        115                 120                 125

Asn Ile Val His Arg Asp Leu Lys Pro His Asn Ile Leu Leu Ser Met
130                 135                 140

Pro Asn Ala His Gly Arg Ile Lys Ala Met Ile Ser Asp Phe Gly Leu
145                 150                 155                 160

Cys Lys Lys Leu Ala Val Gly Arg His Ser Phe Ser Arg Arg Ser Gly
                165                 170                 175

Val Pro Gly Thr Glu Gly Trp Ile Ala Pro Glu Met Leu Ser Glu Asp
            180                 185                 190

Cys Lys Glu Asn Pro Thr Tyr Thr Val Asp Ile Phe Ser Ala Gly Cys
        195                 200                 205

Val Phe Tyr Tyr Val Ile Ser Glu Gly Asn His Pro Phe Gly Lys Ser
210                 215                 220

Leu Gln Arg Gln Ala Asn Ile Leu Leu Gly Ala Cys Ser Leu Asp Cys
225                 230                 235                 240

Phe His Ser Asp Lys His Glu Asp Val Ile Ala Arg Glu Leu Ile Glu
                245                 250                 255

Lys Met Ile Ala Met Asp Pro Gln Gln Arg Pro Ser Ala Lys His Val
            260                 265                 270

Leu Lys His Pro Phe Phe Trp Ser Leu Glu Lys Gln Leu Gln Phe Phe
        275                 280                 285

Gln Asp Val Ser Asp Arg Ile Glu Lys Glu Ser Leu Asp Gly Pro Ile
290                 295                 300

Val Arg Gln Leu Glu Arg Gly Gly Arg Ala Val Val Lys Met Asp Trp
305                 310                 315                 320

Arg Glu Asn Ile Thr Val Pro Leu Gln Thr Asp Leu Arg Lys Phe Arg
                325                 330                 335

Thr Tyr Lys Gly Gly Ser Val Arg Asp Leu Leu Arg Ala Met Arg Asn
            340                 345                 350

Lys Arg His His Tyr Arg Glu Leu Pro Leu Glu Val Gln Glu Thr Leu
        355                 360                 365

Gly Ser Ile Pro Asp Asp Phe Val Arg Tyr Phe Thr Ser Arg Phe Pro
370                 375                 380

His Leu Leu Ser His Thr Tyr Arg Ala Met Glu Leu Cys Arg His Glu
385                 390                 395                 400

Arg Leu Phe Gln Thr Tyr Tyr Trp His Glu Pro Thr Glu Ala Gln Pro
                405                 410                 415

Pro Gly Ile Pro Asp Ala Leu
            420
```

IRE1 SMALL MOLECULE INHIBITORS

CROSS-REFERENCE TO RELATED APPLICATIONS

This application is a U.S. national stage filing under 35 U.S.C. 371 from International Application No. PCT/US2019/063921, filed Dec. 2, 2019, and published as WO 2020/117635 A1 on Jun. 11, 2020, which claims the benefit of priority of U.S. Provisional Application No. 62/774,794, filed Dec. 3, 2018, which is incorporated by reference here in in its entirety for any purpose.

BACKGROUND

Aggressive tumors have evolved strategies that enable them to thrive under constant adverse conditions. For example, cancer cells respond to hypoxia, nutrient starvation, oxidative stress, and high metabolic demand by adjusting their protein folding capacity via the endoplasmic reticulum (ER) stress response pathway. There exists a need for improved methods and compositions to target cancer cells and counter their mechanisms of survival.

BRIEF SUMMARY

Provided in one aspect is a compound of Formula (I), or a pharmaceutically acceptable salt, or solvate thereof:

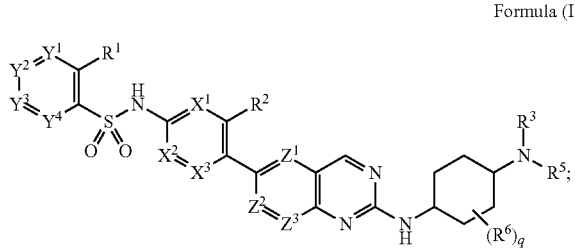

Formula (I)

wherein, $Y^1$, $Y^2$, $Y^3$, and $Y^4$ are each independently selected from N and $CR^8$; $Z^1$ is independently selected from N and $CR^7$; $Z^2$ is independently selected from N and $CR^{7A}$; and $Z^3$ is independently selected from N and $CR^{7B}$; wherein at least one of $Y^1$, $Y^2$, $Y^3$, $Y^4$, $Z^1$, $Z^2$ and $Z^3$ are N and not more than two of $Y^1$, $Y^2$, $Y^3$, and $Y^4$ are N;

$X^1$, $X^2$, and $X^3$ are each independently selected from N and $CR^4$;

$R^1$ is halogen, —CN, —$OR^{10}$, optionally substituted $C_1$-$C_4$alkyl, optionally substituted $C_1$-$C_4$fluoroalkyl, or optionally substituted $C_1$-$C_4$heteroalkyl;

$R^2$ is hydrogen, —CN, —$OR^{10}$, —$SR^{10}$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

$R^3$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^4$ is independently H, halogen, —CN, —S(=O)$R^9$, —S(=O)$_2R^9$, —S(=O)$_2$N($R^{11}$)$_2$, —$NR^{10}$S(=O)$_2R^9$, —C(=O)$R^9$, —OC(=O)$R^9$, —C(=O)$OR^{10}$, —OC(=O)$OR^9$, —N($R^{11}$)$_2$, —OC(=O)N($R^{11}$)$_2$, —$NR^{10}$C(=O)$R^9$, —$NR^{10}$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^5$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^6$ is independently halogen, —CN, —$OR^{10}$, —$SR^{10}$, —S(=O)$R^9$, —S(=O)$_2R^9$, —S(=O)$_2$N($R^{11}$)$_2$, —$NR^{10}$S(=O)$_2R^9$, —C(=O)$R^9$, —OC(=O)$R^9$, —C(=O)$OR^{10}$, —OC(=O)$OR^9$, —N($R^{11}$)$_2$, —OC(=O)N($R^{11}$)$_2$, —$NR^{10}$C(=O)$R^9$, —$NR^{10}$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^7$, $R^{7A}$, and $R^{7B}$ are independently H, —CN, halogen, —$OR^9$, optionally substituted $C_1$-$C_4$alkyl, optionally substituted $C_1$-$C_4$heteroalkyl, optionally substituted $C_1$-$C_4$fluoroalkyl, or optionally substituted aryl;

each $R^8$ is independently H, halogen, —CN, —$OR^{10}$, —$SR^{10}$, —($R^{11}$)$_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^9$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{10}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{11}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^{11}$ are taken together with the N atom to which they are attached to form an optionally substituted heterocycle; and q is 0, 1, 2, 3, or 4.

Any combination of the groups described above or below for the various variables is contemplated herein. Throughout the specification, groups and substituents thereof are chosen by one skilled in the field to provide stable moieties and compounds.

Provided herein are compounds or pharmaceutically acceptable salts, or solvates thereof, that selectively bind to IRE1a at one or more binding sites. In some embodiments, the IRE1a comprises an RNase domain, a kinase domain, or any combination thereof. In some embodiments, the kinase domain is an auto-transphosphorylation kinase domain. In some embodiments, the kinase domain comprises an ATP-binding pocket. In some embodiments, the kinase domain comprises an activation loop. In some embodiments, at least one binding site is within the RNase domain. In some embodiments, at least one binding site is within the kinase domain. In some embodiments, the at least one binding site is within the ATP-binding pocket of the kinase domain. In some embodiments, the at least one binding site is within the activation loop of the kinase domain. In some embodiments, binding occurs at a first binding site. In some embodiments, the first binding site is located within the RNase domain, kinase domain, ATP-binding pocket, or activation loop. In some embodiments, the first binding site comprises at least one amino acid residue of within amino acid residues 465-977 of SEQ ID NO: 1. In some embodiments, the first binding site comprises at least one amino acid residue within amino acid residues 568-833 of SEQ ID NO: 1. In some embodiments, the first binding site comprises at least one amino acid residue within amino acid residues 577-586, 597, 599, 626, 642-643, 645, 648, 688, 692-693, 695, or 711 of SEQ ID NO: 1. In some embodiments, the first binding site comprises at least one amino acid residue within amino acid residues 710-725 or 729-736 of SEQ ID NO: 1. In some embodiments, the first binding site comprises at least one amino acid residue within amino acid residues 835-963 of SEQ ID NO: 1. In some embodiments, binding further occurs at a second binding site. In some embodiments, the second binding site is located within the RNase domain, the kinase domain, the ATP-binding pocket, or the activation loop. In some embodiments, the second binding site comprises at least one amino acid residue of within amino acid residues 465-977 of SEQ ID NO: 1. In some embodiments, the second binding site comprises at least one amino acid residue within amino acid residues 568-833 of SEQ ID NO: 1. In some embodiments, the second binding site comprises at least one amino acid residue within amino acid residues 577-586, 597, 599, 626, 642-643, 645, 648, 688, 692-693, 695, or 711 of SEQ ID NO: 1. In some embodiments, the second binding site comprises at least one amino acid residue within amino acid residues 710-725 or 729-736 of SEQ ID NO: 1. In some embodiments, the second binding site comprises at least one amino acid residue within amino acid residues 835-963 of SEQ ID NO: 1. In some embodiments, binding occurs when the IRE1a is in a homo-dimerized conformation. In some embodiments, binding occurs when the IRE1a is in an oligomerized conformation. In some embodiments, binding occurs when the IRE1a is in a non-oligomerized or non-dimerized conformation. In some embodiments, binding occurs when the IRE1a is in an ATP-bound state. In some embodiments, binding occurs when the IRE1a is in a non-ATP-bound state. In some embodiments, the compound selectively binds to a first IRE1a. In some embodiments, selectively binding to the first IRE1a blocks dimerization of the first IRE1a to a second IRE1a. In some embodiments, selectively binding to the first IRE1a blocks auto-transphosphorylation of the first IRE1a. In some embodiments, selectively binding to the first IRE1a blocks auto-transphosphorylation of a second IRE1a to which the first IRE1a is dimerized. In some embodiments, selectively binding to the first IRE1a blocks activation of the first IRE1a. In some embodiments, selectively binding to the first IRE1a blocks activation a second IRE1a to which the first IRE1a is dimerized. In some embodiments, selectively binding to the first IRE1a blocks kinase activity of the first IRE1a. In some embodiments, selectively binding to the first IRE1a blocks kinase activity of a second IRE1a to which the first IRE1a is dimerized. In some embodiments, selectively binding to the first IRE1a blocks RNase activity of the first IRE1a. In some embodiments, selectively binding to the first IRE1a blocks RNase activity of a second IRE1a to which the first IRE1a is dimerized.

In another aspect, provided herein is a compound that selectively binds a first IRE1a at two or more sites, wherein when the compound is bound to the first IRE1a protein, the compound binds to an ATP-binding pocket of the first IRE1a and blocks the binding of ATP to the first IRE1a. In some embodiments, the ATP binding pocket is comprised within a kinase domain. In some embodiments, the ATP binding pocket is comprised within amino acid residues 465-977 of SEQ ID NO: 1. In some embodiments, the ATP binding pocket is comprised within amino acid residues 568-833 of SEQ ID NO: 1. In some embodiments, the ATP binding pocket comprises one or more of amino acid resides 577-586, 597, 599, 626, 642-643, 645, 648, 688, 692-693, 695, or 711 of SEQ ID NO: 1.

In another aspect, provided herein is a pharmaceutical composition comprising any one of the compounds described herein, or a pharmaceutically acceptable salt or solvate thereof. In some embodiments, the pharmaceutical composition further comprises one or more pharmaceutically acceptable excipients.

In another aspect, provided herein is a method for treating or ameliorating the effects of a disease associated with altered IRE1 signaling, the method comprising administering to a subject in need thereof a pharmaceutical composition, wherein the pharmaceutical composition comprises the compound of any one of the compounds described herein. In some embodiments, the disease is cancer. In some embodiments, the cancer is a solid cancer or a hematologic cancer. In some embodiments, the cancer is an ovarian cancer, a bladder cancer, a breast cancer, or a lung cancer. In some embodiments, the breast cancer is triple negative breast cancer (TNBC). In some embodiments, the cancer is a leukemia, lymphoma, or multiple myeloma. In some embodiments, the pharmaceutical composition administered to the subject intravenously or orally.

In another aspect, provided herein is a method for treating or ameliorating a cell proliferative disorder, the method comprising administering a pharmaceutical composition comprising a compound, or a pharmaceutically acceptable salt, or solvate thereof, that selectively binds to at least one amino acid residue of a IRE1 family protein comprising an RNase domain and kinase domain. In some embodiments, the IRE1 family protein is IRE1a. In some embodiments, the compound binds to an ATP-binding site of IRE1a. In some embodiments, the cell proliferative disorder is cancer. In some embodiments, the cancer is a solid cancer or a hematologic cancer.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Certain Terminology

Figure 1:
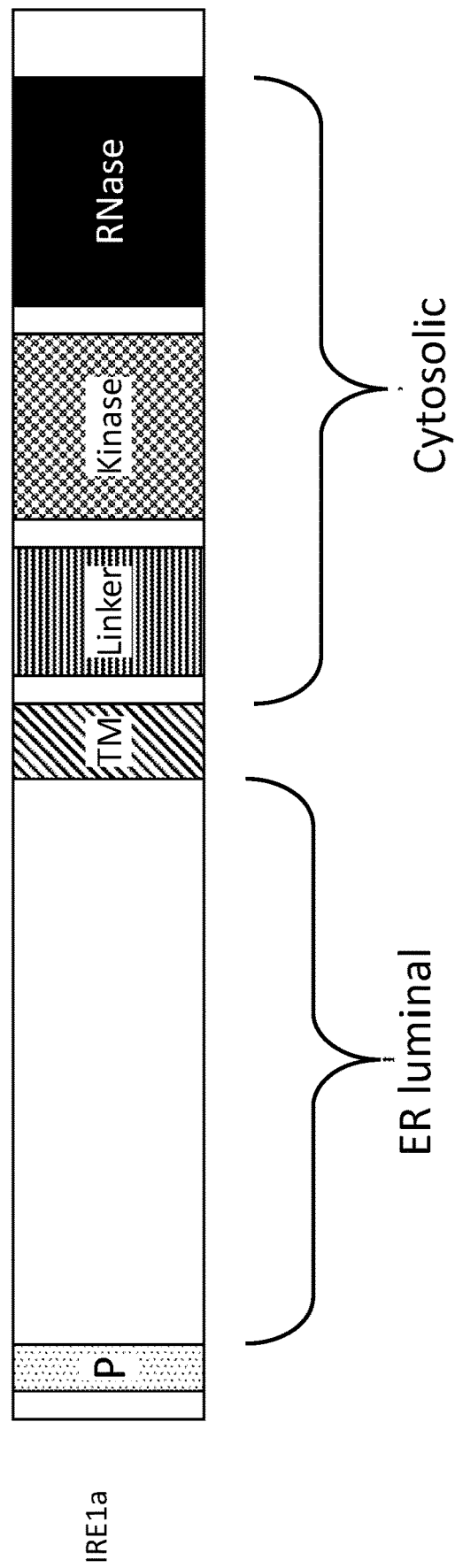
FIG. 1 shows an example diagram of the domain structure of IRE1a. A signal peptide (P) and transmembrane (TM) region are indicated.

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.

"Cyano" refers to the —CN radical.

"Nitro" refers to the —NO$_2$ radical.

"Oxa" refers to the —O— radical.

"Oxo" refers to the =O radical.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. Unless otherwise noted, the "alkyl" group has 1 to 10 carbon atoms, i.e. a $C_1$-$C_{10}$ alkyl, preferably 1 to 6 carbon atoms. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$ alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl. Alkyl includes alkenyls (one or more carbon-carbon double bonds) and alkynyls (one or more carbon-carbon triple bonds).

An "alkylene" group refers refers to a divalent alkyl radical. Any of the above mentioned monovalent alkyl groups may be an alkylene by abstraction of a hydrogen atom from the alkyl. Unless otherwise noted, an alkelene is a $C_1$-$C_6$ alkylene. In other embodiments, an alkylene is a $C_1$-$C_4$ alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —CH$_2$—, —CH(CH$_3$)—, —C(CH$_3$)$_2$—, —CH$_2$CH$_2$—, —CH$_2$CH(CH$_3$)—, —CH$_2$C(CH$_3$)$_2$—, —CH$_2$CH$_2$CH$_2$—, —CH$_2$CH$_2$CH$_2$CH$_2$—, and the like.

An "alkoxy" group refers to a (alkyl)O— group, where alkyl is as defined herein.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. Unless otherwise noted, an aryl is a $C_6$-$C_{10}$ aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Unless otherwise noted, cycloalkyl groups have from 3 to 10 ring atoms, preferably from 3 to 6 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1]pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like.

The term "cycloalkylalkyl" refers to a moiety of the formula —$R_bR_d$ where $R_b$ is an alkylene group as defined herein and $R_d$ is a cycloalkyl moiety as defined herein. In some embodiments, a cycloalkylalkyl moiety is a $C_3$-$C_{10}$cycloalkylalkyl moiety. In such a case, the $C_3$-$C_{10}$cycloalkylalkyl includes a $C_3$-$C_{10}$cycloalkyl radical. In some embodiments, a cycloalkylalkyl moiety is a $C_3$-$C_6$cycloalkylalkyl moiety. In such a case, the $C_3$-$C_6$cycloalkylalkyl includes a $C_3$-$C_6$cycloalkyl radical.

The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoralkyl is a $C_1$-$C_6$ fluoroalkyl.

The term "fluoroalkyl" refers to an alkyl in which one or more hydrogen atoms are replaced by a fluorine atom. In one aspect, a fluoralkyl is a $C_1$-$C_6$ fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to, unless otherwise stated, a straight or branched alkyl group comprising at least one carbon atom and at least one heteroatom, such as O, N (e.g. —NH—, —N(alkyl)-), P, Si, S, and Se. In some embodiments, one or more heteroatoms may be oxidized. Heteroatom(s) may be positioned within the alkyl moiety, e.g., —$CH_2$—O—$CH_2$—; at a point of connectivity with the remainder of the molecule, e.g., —S($=$O)$_2$CH(CH$_3$)CH$_2$—; or a combination thereof, e.g., —NHCH$_2$CH$_2$S($=$O)$_2$CH$_2$—. In one aspect, a heteroalkyl is a $C_1$-$C_6$ heteroalkyl.

As used herein, the term "heteroatom" refers to an atom of any element other than carbon or hydrogen. Unless otherwise noted, the heteroatom is nitrogen, oxygen, or sulfur. In some embodiments, the heteroatom is nitrogen or oxygen. In some embodiments, the heteroatom is nitrogen.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group comprises from 3 to 14 atoms in its ring system comprising 2 to 10 carbon atoms and from one to 4 heteroatoms, and with the proviso that any ring does not contain two adjacent 0 or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo ($=$O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aromatic ring that includes carbon rings atoms and one or more ring heteroatoms selected from nitrogen, oxygen and sulfur. Unless otherwise noted, a heteroaryl has 5 to 10 atoms in its ring system wherein one to four of the ring atoms are heteroatoms and each heteroatom in the ring(s) is selected from O, S and N, with the proviso that any ring does not contain two adjacent O or S atoms. Illustrative examples of heteroaryl groups include monocyclic heteroaryls and bicyclcic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, a heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is a spirocyclic or bridged compound. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

selected from D, halogen, —CN, —NH$_2$, —NH(CH$_3$), —N(CH$_3$)$_2$, —OH, —CO$_2$H, —CO$_2$(C$_1$-C$_4$alkyl), —CH$_2$NH$_2$, —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH (C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O) C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CH$_2$NH$_2$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

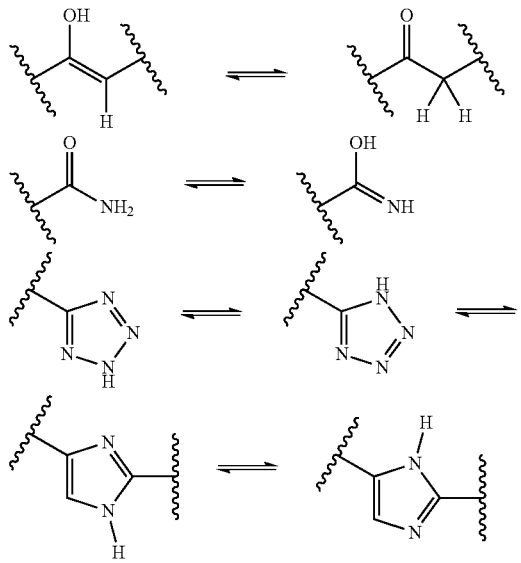
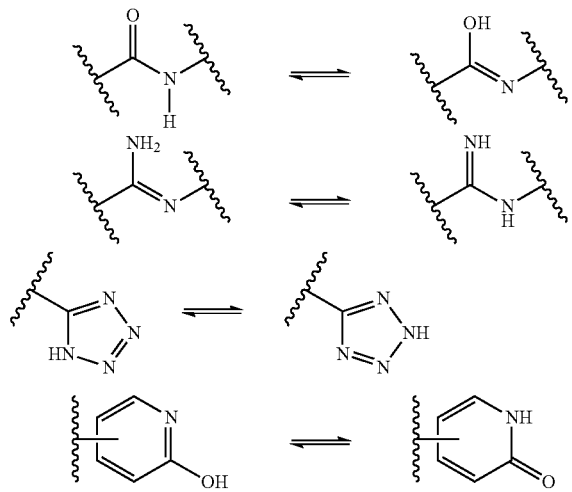

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from deuterium, halogen, —CN, —NH$_2$, —NH (alkyl), —CH$_2$N(alkyl)$_2$, —N(alkyl)$_2$, —OH, —CO$_2$H, —CO$_2$alkyl, —CH$_2$NH$_2$, —C(=O)NH$_2$, —C(=O)NH(alkyl), —C(=O)N(alkyl)$_2$, —S(=O)$_2$NH$_2$, —S(=O)$_2$NH (alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently "Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Compounds

Compounds described herein, including pharmaceutically acceptable salts, and pharmaceutically acceptable solvates thereof, are those that modulate IRE1 mediated signaling, directly or indirectly.

Provided in one aspect is a compound of Formula (I), or a pharmaceutically acceptable salt, or solvate thereof:

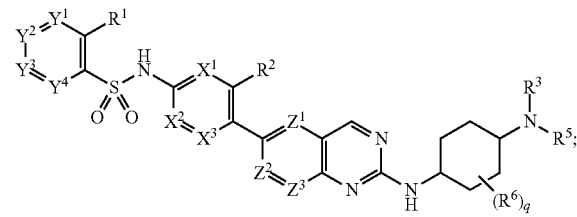

Formula (I)

wherein, $Y^1$, $Y^2$, $Y^3$, and $Y^4$ are each independently selected from N and $CR^8$; $Z^1$ is independently selected from N and $CR^7$; $Z^2$ is independently selected from N and $CR^{7A}$; and $Z^3$ is independently selected from N and $CR^{7B}$; wherein at least one of $Y^1$, $Y^2$, $Y^3$, $Y^4$, $Z^1$, $Z^2$ and $Z^3$ are N and not more than two of $Y^1$, $Y^2$, $Y^3$, and $Y^4$ are N;

$X^1$, $X^2$, and $X^3$ are each independently selected from N and $CR^4$;

$R^1$ is halogen, —CN, —OR$^{10}$, optionally substituted $C_1$-$C_4$alkyl, optionally substituted $C_1$-$C_4$fluoroalkyl, or optionally substituted $C_1$-$C_4$heteroalkyl;

$R^2$ is hydrogen, —CN, —OR$^{10}$, —SR$^{10}$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

$R^3$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^4$ is independently H, halogen, —CN, —OR$^{10}$, —SR$^{10}$, —S(=O)R$^9$, —S(=O)$_2$R$^9$, —S(=O)$_2$N(R$^{11}$)$_2$, —NR$^{10}$S(=O)$_2$R$^9$, —C(=O)R$^9$, —OC(=O)R$^9$, —C(=O)OR$^{10}$, —OC(=O)OR$^9$, —N(R$^{11}$)$_2$, —OC(=O)N(R$^{11}$)$_2$, —NR$^{10}$C(=O)R$^9$, —NR$^{10}$C(=O)OR$^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^5$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^6$ is independently halogen, —CN, —$OR^{10}$, —$SR^{10}$, —S(=O)$R^9$, —S(=O)$_2R^9$, —S(=O)$_2$N$(R^{11})_2$, —$NR^{10}$S(=O)$_2R^9$, —C(=O)$R^9$, —OC(=O)$R^9$, —C(=O)$OR^{10}$, —OC(=O)$OR^9$, —N$(R^{11})_2$, —OC(=O)N$(R^{11})_2$, —$NR^{10}$C(=O)$R^9$, —$NR^{10}$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^7$, $R^{7A}$, and $R^{7B}$ are independently H, —CN, halogen, —$OR^9$, optionally substituted $C_1$-$C_4$alkyl, optionally substituted $C_1$-$C_4$heteroalkyl, optionally substituted $C_1$-$C_4$fluoroalkyl, or optionally substituted aryl;

each $R^8$ is independently H, halogen, —CN, —$OR^{10}$, —$SR^{10}$, —$(R^{11})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^9$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^9$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{10}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{11}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^{11}$ are taken together with the N atom to which they are attached to form an optionally substituted heterocycle; and q is 0, 1, 2, 3, or 4.

Included within compounds of Formula (I) are those of Formula (Ia) or a pharmaceutically salt or solvate thereof wherein $Z^1$, $Z^2$, and $Z^3$ are selected from $CR^7$, $CR^{7A}$, or $CR^{7B}$ respectively as set forth below:

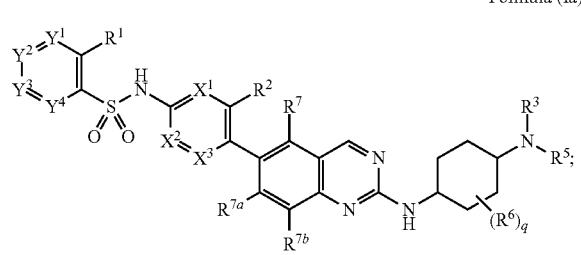

Formula (Ia)

wherein, $Y^1$, $Y^2$, $Y^3$, and $Y^4$ are each independently selected from N and $CR^8$ wherein one or two of $Y^1$, $Y^2$, $Y^3$, and $Y^4$ are N;

$X^1$, $X^2$, and $X^3$ are each independently selected from N and $CR^4$;

$R^1$ is halogen, —CN, —$OR^{10}$, optionally substituted $C_1$-$C_4$alkyl, optionally substituted $C_1$-$C_4$fluoroalkyl, or optionally substituted $C_1$-$C_4$heteroalkyl;

$R^2$ is hydrogen, —CN, —$OR^{10}$, —$SR^{10}$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

$R^3$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^4$ is independently H, halogen, —CN, —$OR^{10}$, —$SR^{10}$, —S(=O)$R^9$, —S(=O)$_2R^9$, —S(=O)$_2$N$(R^{11})_2$, —$NR^{10}$S(=O)$_2R^9$, —C(=O)$R^9$, —OC(=O)$R^9$, —C(=O)$OR^{10}$, —OC(=O)$OR^9$, —N$(R^{11})_2$, —OC(=O)N$(R^{11})_2$, —$NR^{10}$C(=O)$R^9$, —$NR^{10}$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^5$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^6$ is independently halogen, —CN, —$OR^{10}$, —$SR^{10}$, —S(=O)$R^9$, —S(=O)$_2R^9$, —S(=O)$_2$N$(R^{11})_2$, —$NR^{10}$S(=O)$_2R^9$, —C(=O)$R^9$, —OC(=O)$R^9$, —C(=O)$OR^{10}$, —OC(=O)$OR^9$, —N$(R^{11})_2$, —OC(=O)N$(R^{11})_2$, —$NR^{10}$C(=O)$R^9$, —$NR^{10}$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^7$, $R^{7A}$, and $R^{7B}$ are independently H, —CN, halogen, —$OR^9$, optionally substituted $C_1$-$C_4$alkyl, optionally substituted C₁-C₄heteroalkyl, optionally substituted C₁-C₄fluoroalkyl, or optionally substituted aryl;

each R⁸ is independently H, halogen, —CN, —OR¹⁰, —SR¹⁰, —(R¹¹)₂, optionally substituted C₁-C₄alkyl, optionally substituted C₁-C₄fluoroalkyl, optionally substituted C₁-C₄heteroalkyl, optionally substituted C₃-C₆cycloalkyl, optionally substituted C₂-C₁₀heterocycloalkyl, optionally substituted aryl, or optionally substituted heteroaryl;

each R⁹ is independently optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

each R¹⁰ is independently H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

each R¹¹ is independently H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

or two R¹¹ are taken together with the N atom to which they are attached to form an optionally substituted heterocycle; and q is 0, 1, 2, 3, or 4.

Included within compounds of Formula (I) are those of Formula (Ib) or a pharmaceutically salt or solvate thereof wherein Y¹, Y², Y³, and Y⁴ are each CR⁸ as set forth below:

Formula (Ib)

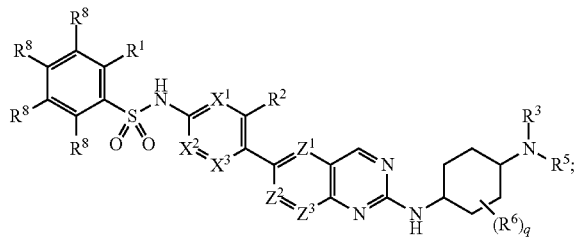

wherein,

Z¹ is independently selected from N or CR⁷, Z² is independently selected from N or CR⁷ᴬ, and Z³ is independently selected from N or CR⁷ᴮ with the proviso that at least one of Z¹, Z², and Z³ are N;

X¹, X², and X³ are each independently selected from N or CR⁴;

R¹ is halogen, —CN, —OR¹⁰, optionally substituted C₁-C₄alkyl, optionally substituted C₁-C₄fluoroalkyl, or optionally substituted C₁-C₄heteroalkyl;

R² is hydrogen, —CN, —OR¹⁰, —SR¹⁰, optionally substituted C₁-C₄alkyl, optionally substituted C₁-C₄fluoroalkyl, optionally substituted —O—C₁-C₄alkyl, optionally substituted C₁-C₄heteroalkyl, optionally substituted C₃-C₆cycloalkyl, optionally substituted —O—C₃-C₆cycloalkyl, optionally substituted C₃-C₆heterocycloalkyl, optionally substituted —O—C₃-C₆heterocycloalkyl, optionally substituted aryl, or optionally substituted heteroaryl;

R³ is H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₃-C₆cyclooalkylalkyl, optionally substituted C₂-C₁₀heterocycloalkyl, optionally substituted aryl, or optionally substituted heteroaryl;

each R⁴ is independently H, halogen, —CN, —OR¹⁰, —SR¹⁰, —S(=O)R⁹, —S(=O)₂R⁹, —S(=O)₂N(R¹¹)₂, —NR¹⁰S(=O)₂R⁹, —C(=O)R⁹, —OC(=O)R⁹, —C(=O)OR¹⁰, —OC(=O)OR⁹, —N(R¹¹)₂, —OC(=O)N(R¹¹)₂, —NR¹⁰C(=O)R⁹, —NR¹⁰C(=O)OR⁹, optionally substituted C₁-C₄alkyl, optionally substituted C₁-C₄fluoroalkyl, optionally substituted C₁-C₄heteroalkyl, optionally substituted C₃-C₆cycloalkyl, optionally substituted aryl, or optionally substituted heteroaryl;

R⁵ is H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₃-C₆cyclooalkylalkyl, optionally substituted C₂-C₁₀heterocycloalkyl, optionally substituted aryl, or optionally substituted heteroaryl;

each R⁶ is independently halogen, —CN, —OR¹⁰, —SR¹⁰, —S(=O)R⁹, —S(=O)₂R⁹, —S(=O)₂N(R¹¹)₂, —NR¹⁰S(=O)₂R⁹, —C(=O)R⁹, —OC(=O)R⁹, —C(=O)OR¹⁰, —OC(=O)OR⁹, —N(R¹¹)₂, —OC(=O)N(R¹¹)₂, —NR¹⁰C(=O)R⁹, —NR¹⁰C(=O)OR⁹, optionally substituted C₁-C₄alkyl, optionally substituted C₁-C₄fluoroalkyl, optionally substituted C₁-C₄heteroalkyl, optionally substituted C₃-C₆cycloalkyl, optionally substituted aryl, or optionally substituted heteroaryl;

R⁷, R⁷ᴬ, and R⁷ᴮ are independently H, —CN, halogen, —OR⁹, optionally substituted C₁-C₄alkyl, optionally substituted C₁-C₄heteroalkyl, optionally substituted C₁-C₄fluoroalkyl, or optionally substituted aryl;

each R⁸ is independently H, halogen, —CN, —OR¹⁰, —SR¹⁰, —(R¹¹)₂, optionally substituted C₁-C₄alkyl, optionally substituted C₁-C₄fluoroalkyl, optionally substituted C₁-C₄heteroalkyl, optionally substituted C₃-C₆cycloalkyl, optionally substituted C₂-C₁₀heterocycloalkyl, optionally substituted aryl, or optionally substituted heteroaryl;

each R⁹ is independently optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

each R¹⁰ is independently H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

each R¹¹ is independently H, optionally substituted C₁-C₄alkyl, optionally substituted C₁-C₄heteroalkyl, optionally substituted C₁-C₄-fluoroalkyl, optionally substituted C₃-C₆cycloalkyl, optionally substituted C₂-C₁₀-heterocycloalkyl, optionally substituted aryl, or optionally substituted heteroaryl;

or two R¹¹ are taken together with the N atom to which they are attached to form an optionally substituted heterocycle; and q is 0, 1, 2, 3, or 4.

Included within compounds of Formula (I) are those of Formula (Ic) or a pharmaceutically salt or solvate thereof:

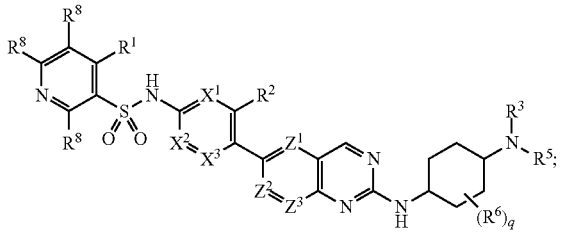

Formula (Ic)

wherein, $Z^1$ is independently selected from N or $CR^7$, $Z^2$ is independently selected from N or $CR^{7A}$, and $Z^3$ is independently selected from N or $CR^{7B}$;

$X^1$, $X^2$, and $X^3$ are each independently selected from N or $CR^4$;

$R^1$ is halogen, —CN, —$OR^{10}$, optionally substituted $C_1$-$C_4$alkyl, optionally substituted $C_1$-$C_4$fluoroalkyl, or optionally substituted $C_1$-$C_4$heteroalkyl;

$R^2$ is hydrogen, —CN, —$OR^{10}$, —$SR^{10}$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

$R^3$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^4$ is independently H, halogen, —CN, —$OR^{10}$, —$SR^{10}$, —S(=O)$R^9$, —S(=O)$_2R^9$, —S(=O)$_2$N($R^{11}$)$_2$, —$NR^{10}$S(=O)$_2R^9$, —C(=O)$R^9$, —OC(=O)$R^9$, —C(=O)$OR^{10}$, —OC(=O)$OR^9$, —N($R^{11}$)$_2$, —OC(=O)N($R^{11}$)$_2$, —$NR^{10}$C(=O)$R^9$, —$NR^{10}$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^5$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^6$ is independently halogen, —CN, —$OR^{10}$, —$SR^{10}$, —S(=O)$R^9$, —S(=O)$_2R^9$, —S(=O)$_2$N($R^{11}$)$_2$, —$NR^{10}$S(=O)$_2R^9$, —C(=O)$R^9$, —OC(=O) $R^9$, —C(=O)$OR^{10}$, —OC(=O)$OR^9$, —N($R^{11}$)$_2$, —OC(=O)N($R^{11}$)$_2$, —$NR^{10}$C(=O)$R^9$, —$NR^{10}$C(=O)$OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^7$, $R^{7A}$, and $R^{7B}$ are independently H, —CN, halogen, —$OR^9$, optionally substituted $C_1$-$C_4$alkyl, optionally substituted $C_1$-$C_4$heteroalkyl, optionally substituted $C_1$-$C_4$fluoroalkyl, or optionally substituted aryl;

each $R^8$ is independently H, halogen, —CN, —$OR^{10}$, —$SR^{10}$, —($R^{11}$)$_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each $R^9$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{10}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{11}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^{11}$ are taken together with the N atom to which they are attached to form an optionally substituted heterocycle; and q is 0, 1, 2, 3, or 4.

Included within compounds of Formula (I) are those of Formula (Id) or a pharmaceutically salt or solvate thereof:

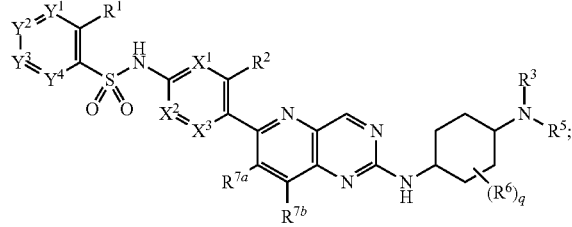

Formula (Id)

wherein, $Y^1$, $Y^2$, $Y^3$, and $Y^4$ are each independently selected from N and $CR^8$ wherein one or two of $Y^1$, $Y^2$, $Y^3$, and $Y^4$ are N;

$X^1$, $X^2$, and $X^3$ are each independently selected from N and $CR^4$;

$R^1$ is halogen, —CN, —$OR^{10}$, optionally substituted $C_1$-$C_4$alkyl, optionally substituted $C_1$-$C_4$fluoroalkyl, or optionally substituted $C_1$-$C_4$heteroalkyl;

$R^2$ is hydrogen, —CN, —$OR^{10}$, —$SR^{10}$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

R³ is H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₃-C₆cyclooalkylalkyl, optionally substituted C₂-C₁₀heterocycloalkyl, optionally substituted aryl, or optionally substituted heteroaryl;

each R⁴ is independently H, halogen, —CN, —OR¹⁰, —SR¹⁰, —S(=O)R⁹, —S(=O)₂R⁹, —S(=O)₂N(R¹¹)₂, —NR¹⁰S(=O)₂R⁹, —C(=O)R⁹, —OC(=O)R⁹, —C(=O)OR¹⁰, —OC(=O)OR⁹, —N(R¹¹)₂, —OC(=O)N(R¹¹)₂, —NR¹⁰C(=O)R⁹, —NR¹⁰C(=O)OR⁹, optionally substituted C₁-C₄alkyl, optionally substituted C₁-C₄fluoroalkyl, optionally substituted C₁-C₄heteroalkyl, optionally substituted C₃-C₆cycloalkyl, optionally substituted aryl, or optionally substituted heteroaryl;

R⁵ is H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₃-C₆cyclooalkylalkyl, optionally substituted C₂-C₁₀heterocycloalkyl, optionally substituted aryl, or optionally substituted heteroaryl;

each R⁶ is independently halogen, —CN, —OR¹⁰, —SR¹⁰, —S(=O)R⁹, —S(=O)₂R⁹, —S(=O)₂N(R¹¹)₂, —NR¹⁰S(=O)₂R⁹, —C(=O)R⁹, —OC(=O)R⁹, —C(=O)OR¹⁰, —OC(=O)OR⁹, —N(R¹¹)₂, —OC(=O)N(R¹¹)₂, —NR¹⁰C(=O)R⁹, —NR¹⁰C(=O)OR⁹, optionally substituted C₁-C₄alkyl, optionally substituted C₁-C₄fluoroalkyl, optionally substituted C₁-C₄heteroalkyl, optionally substituted C₃-C₆cycloalkyl, optionally substituted aryl, or optionally substituted heteroaryl;

R⁷, R⁷ᴬ, and R⁷ᴮ are independently H, —CN, halogen, —OR⁹, optionally substituted C₁-C₄alkyl, optionally substituted C₁-C₄heteroalkyl, optionally substituted C₁-C₄fluoroalkyl, or optionally substituted aryl;

each R⁸ is independently H, halogen, —CN, —OR¹⁰, —SR¹⁰, —(R¹¹)₂, optionally substituted C₁-C₄alkyl, optionally substituted C₁-C₄fluoroalkyl, optionally substituted C₁-C₄heteroalkyl, optionally substituted C₃-C₆cycloalkyl, optionally substituted C₂-C₁₀heterocycloalkyl, optionally substituted aryl, or optionally substituted heteroaryl;

each R⁹ is independently optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

each R¹⁰ is independently H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

each R¹¹ is independently H, optionally substituted C₁-C₄alkyl, optionally substituted C₁-C₄heteroalkyl, optionally substituted C₁-C₄fluoroalkyl, optionally substituted C₃-C₆cycloalkyl, optionally substituted C₂-C₁₀heterocycloalkyl, optionally substituted aryl, or optionally substituted heteroaryl;

or two R¹¹ are taken together with the N atom to which they are attached to form an optionally substituted heterocycle; and q is 0, 1, 2, 3, or 4.

In Formulas (I), (Ia), (Ib), (Ic), (Id),

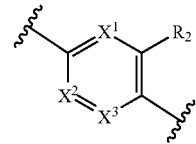

are, for example,

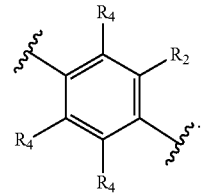

In such embodiments, R¹, R², R³, R⁴, R⁵, R⁶, R⁷, R⁷ᴬ, R⁷ᴮ, R⁸, R⁹, R¹⁰, Y¹, Y², Y³, Y⁴, Z¹, Z², Z³, and q are as defined above for Formulas (I), (Ia), (Ib), (Ic), or (Id), or are as defined in any of the embodiments described herein for those substituents in any combination thereof.

In Formulas (I), (Ia), (Ib), (Ic), (Id),

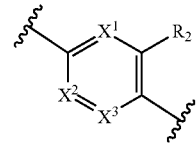

are, for example,

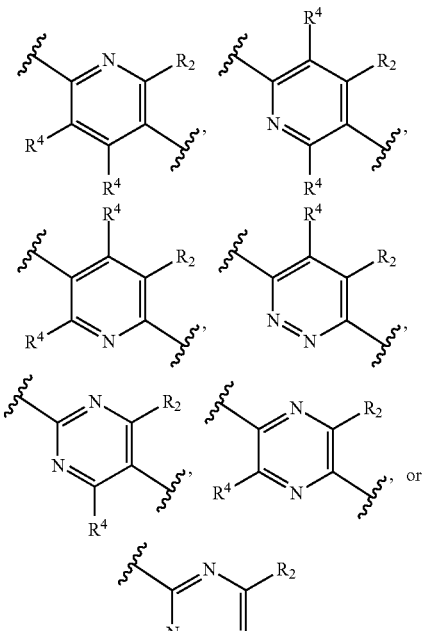

In such embodiments, $R^1$, $R^2$, $R^3$, $R^4$, $R^5$, $R^6$, $R^7$, $R^{7A}$, $R^{7B}$, $R^8$, $R^9$, $R^{10}$, $Y^1$, $Y^2$, $Y^3$, $Y^4$, $Z^1$, $Z^2$, $Z^3$, and q are as defined above for Formulas (I), (Ia), (Ib), (Ic), or (Id), or are as defined in any of the embodiments described herein for those substituents in any combination thereof.

In some embodiments,

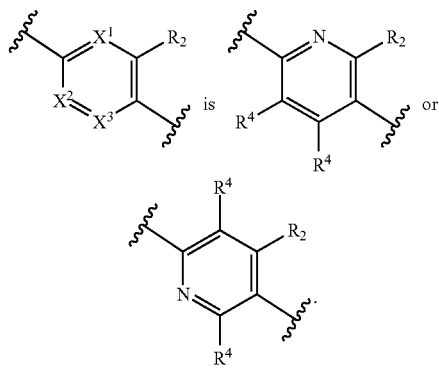

In such embodiments, $R^1$, $R^2$, $R^3$, $R^4$, $R^5$, $R^6$, $R^7$, $R^{7A}$, $R^{7B}$, $R^8$, $R^9$, $R^{10}$, $Y^1$, $Y^2$, $Y^3$, $Y^4$, $Z^1$, $Z^2$, $Z^3$, and q are as defined above for Formulas (I), (Ia), (Ib), (Ic), or (Id), or are as defined in any of the embodiments described herein for those substituents in any combination thereof.

In some embodiments,

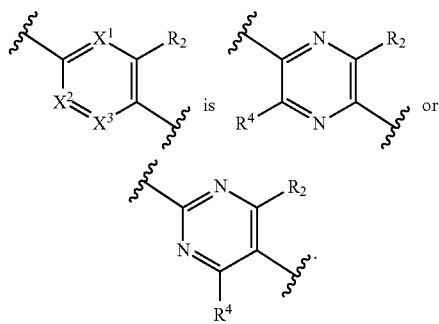

In such embodiments, $R^1$, $R^2$, $R^3$, $R^4$, $R^5$, $R^6$, $R^7$, $R^{7A}$, $R^{7B}$, $R^8$, $R^9$, $R^{10}$, $Y^1$, $Y^2$, $Y^3$, $Y^4$, $Z^1$, $Z^2$, $Z^3$, and q are as defined above for Formulas (I), (Ia), (Ib), (Ic), or (Id), or are as defined in any of the embodiments described herein for those substituents in any combination thereof.

In some embodiments,

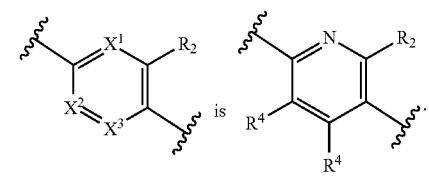

In such embodiments, $R^1$, $R^2$, $R^3$, $R^4$, $R^5$, $R^6$, $R^7$, $R^{7A}$, $R^{7B}$, $R^8$, $R^9$, $R^{10}$, $Y^1$, $Y^2$, $Y^3$, $Y^4$, $Z^1$, $Z^2$, $Z^3$, and q are as defined above for Formulas (I), (Ia), (Ib), (Ic), or (Id), or are as defined in any of the embodiments described herein for those substituents in any combination thereof.

In some embodiments, each $R^4$ is independently H, halogen, —CN, —$OR^8$, optionally substituted $C_1$-$C_4$alkyl, optionally substituted $C_1$-$C_4$fluoroalkyl, or optionally substituted $C_1$-$C_4$heteroalkyl. In some embodiments, each $R^4$ is independently H, halogen, —CN, or optionally substituted $C_1$-$C_4$alkyl. In some embodiments, each $R^4$ is independently H, fluorine, chlorine, —CN, or unsubstituted $C_1$-$C_4$alkyl. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $Y^1$, $Y^2$, $Y^3$, $Y^4$, $Z^1$, $Z^2$, $Z^3$, and q are as defined above for Formulas (I), (IA), (Ib), (Ic), or (Id), or are as defined in any of the embodiments described herein for those substituents in any combination thereof.

Further compounds described herein include those wherein $X^1$ is nitrogen, and $X^2$ and $X^3$ are CH as set forth in structure of formula (I'), (Ia'), (Ib'), (Ic'), or (Id') or a pharmaceutically acceptable salt or solvate thereof:

(I')

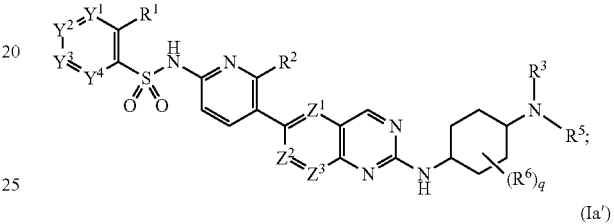

(Ia')

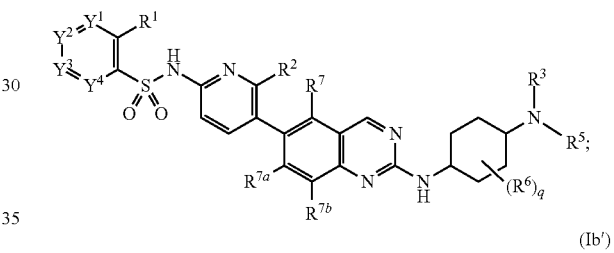

(Ib')

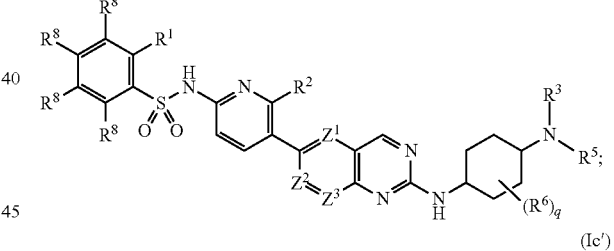

(Ic')

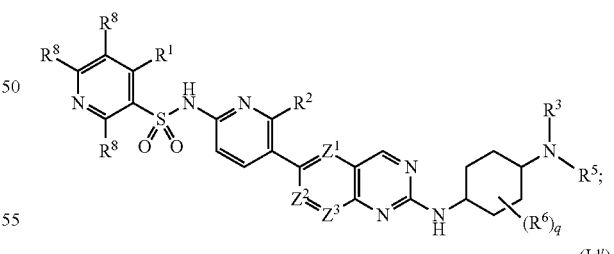

(Id')

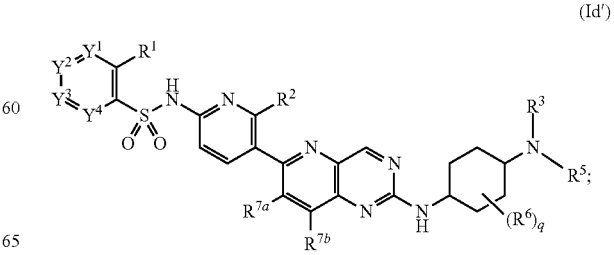

wherein $R^1$, $R^2$, $R^3$, $R^4$, $R^5$, $R^6$, $R^7$, $R^{7A}$, $R^{7B}$, $R^8$, $R^9$, $R^{10}$, $Y^1$, $Y^2$, $Y^3$, $Y^4$, $Z^1$, $Z^2$, $Z^3$, and q are as defined above for Formulas (I), (Ia), (Ib), (Ic), and (Id) respectively.

In some embodiments, $R^2$ is —CN, —$OR^{10}$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, or optionally substituted —O—$C_3$-$C_6$cycloalkyl. In some embodiments, $R^2$ is optionally substituted $C_1$-$C_4$alkyl or optionally substituted —O—$C_1$-$C_4$alkyl. In some embodiments, $R^2$ is unsubstituted $C_1$-$C_4$alkyl or unsubstituted —O—$C_1$-$C_4$alkyl. In some embodiments, $R^2$ is methyl or methoxy. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, $R^{10}$ is optionally substituted $C_1$-$C_4$alkyl, optionally substituted $C_1$-$C_4$heteroalkyl, optionally substituted $C_1$-$C_4$fluoroalkyl, or optionally substituted $C_3$-$C_6$cycloalkyl. In all such embodiments, $R^1$, $R^2$, $R^3$, $R^4$, $R^5$, $R^6$, $R^7$, $R^{7A}$, $R^{7B}$, $R^8$, $R^9$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, $R^9$ is optionally substituted $C_1$-$C_4$alkyl, optionally substituted $C_1$-$C_4$heteroalkyl, optionally substituted $C_1$-$C_4$fluoroalkyl, or optionally substituted $C_3$-$C_6$cycloalkyl. In all such embodiments, $R^1$, $R^2$, $R^3$, $R^4$, $R^5$, $R^6$, $R^7$, $R^{7A}$, $R^{7B}$, $R^8$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, $R^1$ is halogen, —CN, —$OR^8$, optionally substituted $C_1$-$C_4$alkyl, or optionally substituted $C_1$-$C_4$fluoroalkyl. In some embodiments, $R^1$ is halogen or optionally substituted $C_1$-$C_4$alkyl. In some embodiments, $R^1$ is chlorine, fluorine or unsubstituted $C_1$-$C_4$alkyl. In some embodiments, $R^1$ is chlorine. In all such embodiments, $R^2$, $R^3$, $R^4$, $R^5$, $R^6$, $R^7$, $R^{7A}$, $R^{7B}$, $R^8$, $R^9$, $R^{10}$, $X_1$, $X_2$, $X_3$, $Y_1$, $Y_2$, $Y_3$, $Y_4$, $Z_1$, $Z_2$, $Z_3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, each $R^8$ is independently H, halogen, —CN, —$OR^{10}$, —$SR^{10}$, —$N(R^{11})_2$, optionally substituted $C_1$-$C_4$alkyl, or optionally substituted $C_1$-$C_4$fluoroalkyl. In some embodiments, each $R^8$ is independently H, halogen, —CN, or optionally substituted $C_1$-$C_4$alkyl. In some embodiments, each $R^8$ is independently H, fluorine, chlorine, —CN, or unsubstituted $C_1$-$C_4$alkyl. In some embodiments, each $R^8$ is H. In all such embodiments, $R^1$, $R^2$, $R^3$, $R^4$, $R^5$, $R^6$, $R^7$, $R^{7A}$, $R^{7B}$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, each $R^6$ is independently halogen, —$OR^{10}$, optionally substituted $C_1$-$C_4$alkyl, optionally substituted $C_1$-$C_4$heteroalkyl, or optionally substituted $C_1$-$C_4$fluoroalkyl. In some embodiments, each $R^6$ is independently halogen, —OH, or optionally substituted $C_1$-$C_4$alkyl. In some embodiments, each $R^6$ is independently fluorine, —OH, or unsubstituted $C_1$-$C_4$alkyl. In some embodiments, $R^6$ is absent. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, q is 0, 1, 2, or 3. In some embodiments, q is 0, 1, or 2. In some embodiments, q is 0 or 1. In some embodiments, q is 0. In some embodiments, q is 1. In some embodiments, q is 2. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, and $Z^3$, are as defined above for Formulas (I), (Ia), (Ib), (Ic), (Id), (I'), (Ia'), (Ib), (Ic') or (Id') or are as defined in any of the embodiments described herein for those substituents in any combination thereof.

In some embodiments, $R^3$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cyclooalkyl, or optionally substituted $C_3$-$C_6$cycloalkylalkyl. In some embodiments, $R^3$ is H or optionally substituted $C_1$-$C_4$alkyl. In some embodiments, $R^3$ is H or unsubstituted $C_1$-$C_4$alkyl. In some embodiments, $R^3$ is H or methyl or ethyl. In some embodiments, $R^3$ is H or methyl. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, and $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, $R^5$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cyclooalkyl, or optionally substituted $C_3$-$C_6$cycloalkylalkyl. In some embodiments, $R^5$ is H or optionally substituted $C_1$-$C_4$alkyl. In some embodiments, $R^5$ is H or unsubstituted $C_1$-$C_4$alkyl. In some embodiments, $R^5$ is H or methyl or ethyl. In some embodiments, $R^5$ is H or methyl. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, and $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, $R^7$ is H, halogen, —CN, optionally substituted $C_1$-$C_4$alkyl, optionally substituted $C_1$-$C_4$heteroalkyl, or optionally substituted $C_1$-$C_4$fluoroalkyl. In some embodiments, $R^{7A}$ is H, halogen, —CN, optionally substituted $C_1$-$C_4$alkyl. In some embodiments, $R^{7A}$ is H, fluorine, chlorine, —CN, or unsubstituted $C_1$-$C_4$alkyl. In some embodiments, $R^{7A}$ is H. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, $R^{7A}$ is H, halogen, —CN, optionally substituted $C_1$-$C_4$alkyl, optionally substituted $C_1$-$C_4$heteroalkyl, or optionally substituted $C_1$-$C_4$fluoroalkyl. In some embodiments, $R^{7A}$ is H, halogen, —CN, optionally substituted $C_1$-$C_4$alkyl. In some embodiments, $R^{7A}$ is H, fluorine, chlorine, —CN, or unsubstituted $C_1$-$C_4$alkyl. In some embodiments, $R^{7A}$ is H. In all such embodiments, $R^1$, $R^2$, $R^3$, $R^4$, $R^5$, $R^6$, $R^7$, $R^{7B}$, $R^8$, $R^9$, $R^{10}$, $X^1$, $X^2$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, $R^{7B}$ is H, halogen, —CN, optionally substituted $C_1$-$C_4$alkyl, optionally substituted $C_1$-$C_4$heteroalkyl, or optionally substituted $C_1$-$C_4$fluoroalkyl. In some embodiments, $R^{7B}$ is H, halogen, —CN, optionally substituted $C_1$-$C_4$alkyl. In some embodiments, $R^{7B}$ is H, fluorine, chlorine, —CN, or unsubstituted $C_1$-$C_4$alkyl. In some embodiments, $R^{7B}$ is unsubstituted $C_1$-$C_4$alkyl. In some embodiments, $R^{7B}$ is ethyl. In all such embodiments, $R^1$, $R^2$, $R^3$, $R^4$, $R^5$, $R^6$, $R^7$, $R^{7A}$, $R^8$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments each $R^9$ is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, or optionally substituted $C_2$-$C_{10}$heterocycloalkyl. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, each $R^{10}$ is independently hydrogen, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, or optionally substituted $C_2$-$C_{10}$heterocycloalkyl. In all such embodiments, $R^1$, $R^2$, $R^3$, $R^4$, $R^5$, $R^6$, $R^7$, $R^{7A}$, $R^{7B}$, $R^8$, $R^9$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —CH$_2$NH$_2$, —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CH$_2$NH$_2$, —CF$_3$, —OCH$_3$, and —OCF$_3$. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some embodiments, there are no optional substituents. In all such embodiments, $R^1$, $R^2$, $R^3$, $R^4$, $R^5$, $R^6$, $R^7$, $R^{7A}$, $R^{7B}$, $R^8$, $R^9$, $R^{10}$, $X^1$, $X^2$, $X^3$, $Y^1$, $Y^2$, $Y^3$, $Y^4$, $Z^1$, $Z^2$, $Z^3$, and q are as defined above for Formulas (I), (Ia), (Ib), (Ic), (Id), (I'), (Ia'), (Ib'), (Ic') or (Id') or are as defined in any of the embodiments described herein for those substituents in any combination thereof.

In some such aspects of Formulas (I), (Ia), (Ib), (Ic), (Id), (I'), (Ia'), (Ib'), (Ic') or (Id') or a pharmaceutically acceptable salt or solvate thereof;
  $R^1$ is chlorine, fluorine or unsubstituted $C_1$-$C_4$alkyl;
  $R^2$ is unsubstituted $C_1$-$C_4$alkyl or unsubstituted —O—$C_1$-$C_4$alkyl;
  $R^3$ is hydrogen or unsubstituted $C_1$-$C_4$alkyl;
  each $R^4$ is independently selected from hydrogen, fluorine, chlorine, —CN, and unsubstituted $C_1$-$C_4$alkyl;
  $R^5$ is hydrogen or unsubstituted $C_1$-$C_4$alkyl
  each $R^6$ is independently selected from fluorine, —OH, and unsubstituted $C_1$-$C_4$alkyl and q is 0, 1, or 2;
  $Z^1$ is N or $CR^7$ wherein $R^7$ is hydrogen, fluorine, chlorine, —CN or unsubstituted $C_1$-$C_4$alkyl;
  $Z^2$ is N or $CR^{7A}$ wherein $R^{7A}$ is hydrogen, fluorine, chlorine, —CN or unsubstituted $C_1$-$C_4$alkyl;
  $Z^3$ is N or $CR^{7B}$ wherein $R^{7B}$ is hydrogen, fluorine, chlorine, —CN or unsubstituted $C_1$-$C_4$alkyl;
  $Y^1$ is N or $CR^8$;
  $Y^2$ is N or $CR^8$;
  $Y^3$ is N or $CR^8$;
  $Y^4$ is N or $CR^8$;
  each $R^8$ is independently selected from hydrogen, fluorine, chlorine, —CN or unsubstituted $C_1$-$C_4$alkyl;
  $X^1$ is N or $CR^4$;
  $X^2$ is N or $CR^4$; and
  $X^3$ is N or $CR^4$; with the proviso that at least one of $Y^1$, $Y^2$, $Y^3$, $Y^4$, $Z^1$, $Z^2$, and $Z^3$ are N, and not more than two of $Y^1$, $Y^2$, $Y^3$, and $Y^4$ are N. In some such aspects at least one of $X^1$, $X^2$, and $X^3$ are N. In other aspects, $X^1$, $X^2$, and $X^3$ are $CR^4$.

In some such aspects of Formulas (I), (Ia), (Ib), (Ic), (Id), (I'), (Ia'), (Ib'), (Ic') or (Id') or a pharmaceutically acceptable salt or solvate thereof;
  $R^1$ is chlorine;
  $R^2$ is unsubstituted $C_1$-$C_4$alkyl or unsubstituted —O—$C_1$-$C_4$alkyl;
  $R^3$ is hydrogen or unsubstituted $C_1$-$C_4$alkyl;
  $R^4$ is hydrogen;
  $R^5$ is hydrogen or unsubstituted $C_1$-$C_4$alkyl
  $R^6$ is absent as q is zero;
  $Z^1$ is N or $CR^7$ wherein $R^7$ is H;
  $Z^2$ is N or $CR^{7A}$ wherein $R^{7A}$ is H;
  $Z^3$ is N or $CR^{7B}$ wherein $R^{7B}$ is unsubstituted $C_1$-$C_4$alkyl;
  $Y^1$ is N or $CR^8$;
  $Y^2$ is N or $CR^8$;
  $Y^3$ is N or $CR^8$;
  $Y^4$ is N or $CR^8$;
  $R^8$ is hydrogen;
  $X^1$ is N or $CR^4$;
  $X^2$ is N or $CR^4$; and
  $X^3$ is N or $CR^4$; with the proviso that at least one of $Y^1$, $Y^2$, $Y^3$, $Y^4$, $Z^1$, $Z^2$, and $Z^3$ are N and not more than two of $Y^1$, $Y^2$, $Y^3$, and $Y^4$ are N. In some such aspects at least one of $X^1$, $X^2$, and $X^3$ are N. In other aspects, $X^1$, $X^2$, and $X^3$ are $CR^4$.

In some such aspects of Formulas (I), (Ia), (Ib), (Ic), (Id), (I'), (Ia'), (Ib), (Ic') or (Id') or a pharmaceutically acceptable salt or solvate thereof;
  $R^1$ is chlorine;
  $R^2$ is methyl or methoxy;
  $R^3$ is hydrogen or methyl;
  $R^4$ is hydrogen;
  $R^5$ is hydrogen or methyl;

R⁶ is absent as q is zero;
Z₁ is N or CR⁷ wherein R⁷ is H;
Z₂ is N or CR⁷ᴬ wherein R⁷ᴬ is H;
Z₃ is N or CR⁷ᴮ wherein R⁷ᴮ is ethyl;
Y₁ is N or CR⁸;
Y₂ is N or CR⁸;
Y₃ is N or CR⁸;
Y₄ is N or CR⁸;
R⁸ is hydrogen;
X₁ is N or CR⁴;
X₂ is N or CR⁴; and
X₃ is N or CR⁴; with the proviso that at least one of Y¹, Y², Y³, Y⁴, Z¹, Z² and Z³ are N and not more than two of Y¹, Y², Y³, and Y⁴ are N. In some such aspects at least one of X¹, X², and X³ are N. In other aspects, X¹, X², and X³ are CR⁴.

In particular embodiments, the compounds described herein are in the trans-configuration. The trans-configuration for formula (I) is as shown below:

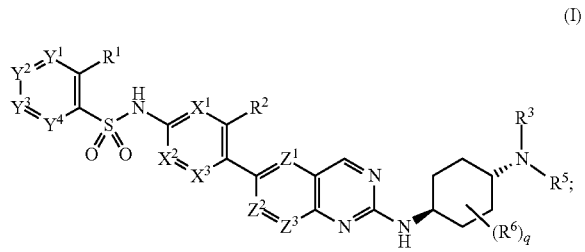

(I)

In some embodiments, a compound described herein is selected from any one of the compounds from Table 1.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reac-

TABLE 1

| Compound No. | Structure | Name |
|---|---|---|
| 1 | 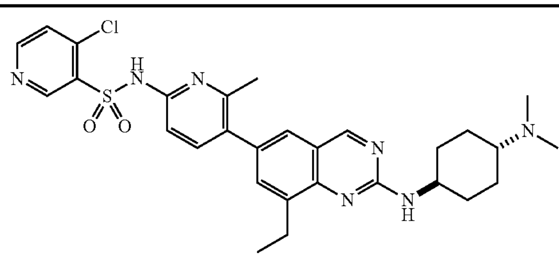 | 4-chloro-N-(5-(2-(((1r,4r)-4-(dimethylamino)cyclohexyl)-amino)-8-ethylquinazolin-6-yl)-6-methylpyridin-2-yl)-pyridine-3-sulfonamide |
| 2 | 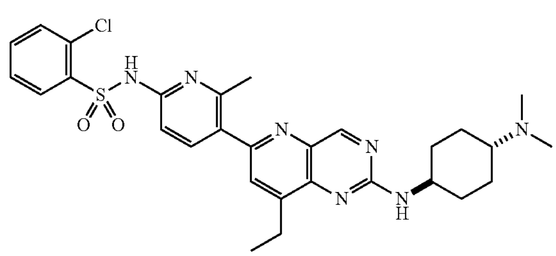 | 2-chloro-N-(5-(2-(((1r,4r)-4-(dimethylamino)cyclohexyl)-amino)-8-ethylpyrido[3,2-d]-pyrimidin-6-yl)-6-methyl-pyridin-2-yl)benzenesulfon-amide |

In one aspect, provided herein is a pharmaceutically acceptable salt or solvate thereof of a compound described in Table 1. Any combination of the groups described above or below for the various variables is contemplated herein. Throughout the specification, groups and substituents thereof are chosen by one skilled in the field to provide stable moieties and compounds.

tivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, prodrugs, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. Also described herein are methods of treating diseases by administering such prodrugs. Further described herein are methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds described herein. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

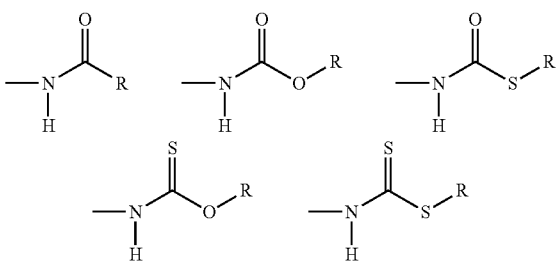

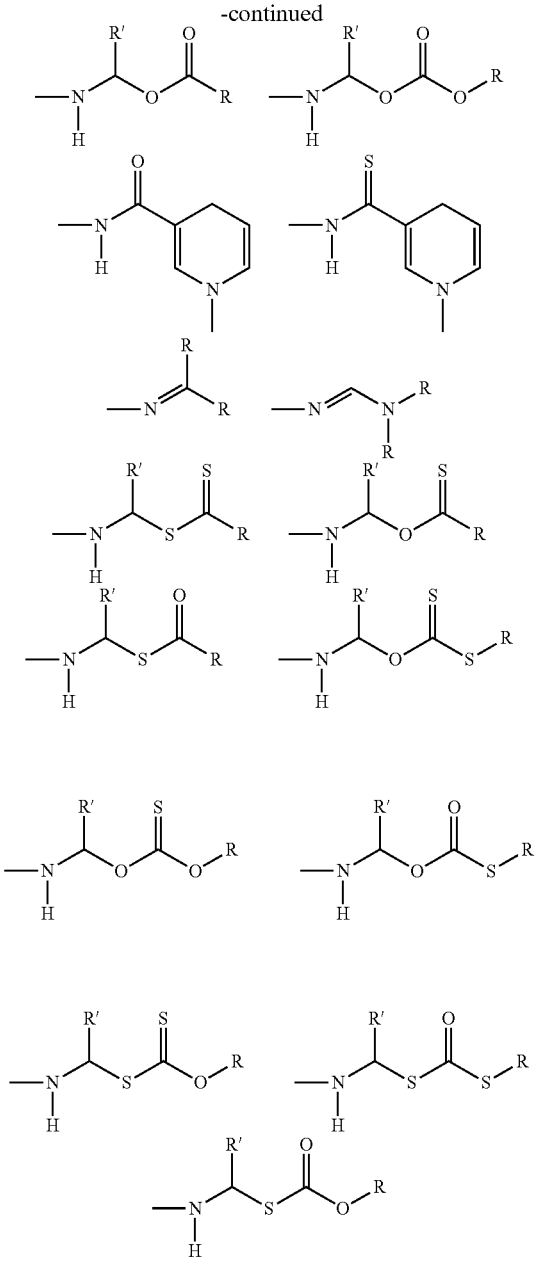

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

IRE1-Like Family of Proteins

In some embodiments, a compound disclosed herein selectively binds to a protein of the serine/threonine-protein kinase/endoribonuclease inositol-requiring enzyme 1 (IRE1) family of proteins. In humans, IRE1 is encoded by the ERN1 gene. Exemplary IRE1 family proteins include isoforms IRE1 and IRE1a. Other exemplary IRE1 family proteins include IRE1 homologues or orthologues in other organisms. Exemplary organisms include human, non-human primate, mouse, rat, chicken, fruit fly, yeast, and others listed in Table 2. In some embodiments, the IRE1 protein is human IRE1a.

TABLE 2

| Organism | Accession # |
|---|---|
| Homo sapiens | NP_001424.3 |
| Mus musculus | NP_076402.1 |
| Rattus norvegicus | XP_006247696.1 |

Figure 2:
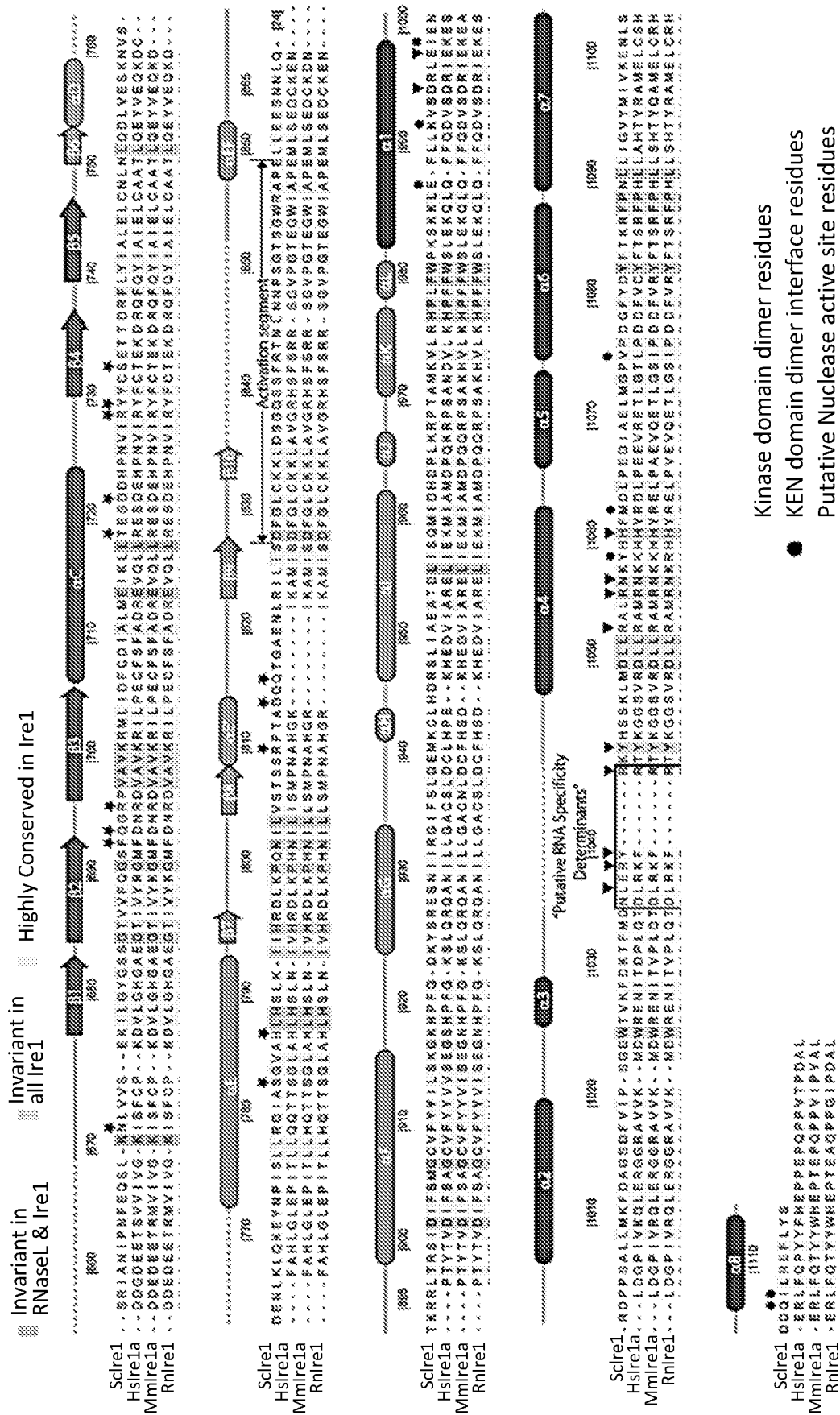
FIG. 2 shows an example alignment of the C-terminal half IRE1 orthologues from yeast (ScIre1), human (HsIre1), mouse (MmIre1), and rat (RnIRE1). Stars indicate kinase domain dimer interface residues. Circles indicate Kinase extension nuclease (KEN) domain dimer interface residues. Triangles indicate putative nuclease active site residues.

In some embodiments, a compound disclosed herein selectively binds to an IRE1 family protein comprising a kinase domain and/or an RNase domain. In some embodiments, the kinase domain is a trans-autophosphorylation kinase domain. In some embodiments, the IRE1 family protein is IRE1a. An example arrangement of domains within an IRE1a protein is depicted in FIG. 1. An example alignment of IRE1 family protein orthologues is depicted in FIG. 2.

In some embodiments, a compound disclosed herein selectively binds to a trans-autophosphorylation kinase domain region of IRE1a. In some embodiments, a compound disclosed herein selectively binds to a trans-autophosphorylation kinase domain region of IRE1a, for example within amino acid residues 568-833 of SEQ ID NO: 1, or equivalent amino acid residues thereof.

In some embodiments, a compound disclosed herein selectively binds to an ATP-binding pocket within a trans-autophosphorylation kinase domain region of IRE1a. In some embodiments, a compound disclosed herein selectively binds to an ATP-binding pocket within a trans-autophosphorylation kinase domain region of IRE1a, for example, one or more of amino acid resides 577-711, 577-586, 597, 599, 626, 642-643, 645, 648, 688, 692-693, 695, or 711 of SEQ ID NO: 1, or equivalent amino acid residues thereof.

In some embodiments, a compound disclosed herein selectively binds to an activation loop within a trans-autophosphorylation kinase domain region of IRE1a. In some embodiments, a compound disclosed herein selectively binds to an activation loop within a trans-autophosphorylation kinase domain region of IRE1a, for example, one or more of amino acid residues 710-736, 710-725, or 729-736 of SEQ ID NO: 1, or equivalent amino acid residues thereof.

In some embodiments, a compound disclosed herein selectively binds to an RNase domain region of IRE1a. In some embodiments, a compound disclosed herein selectively binds to an RNase domain region of IRE1a, for example within amino acid residues 835-963 of SEQ ID NO: 1, or equivalent amino acid residues thereof.

In some embodiments, a compound disclosed herein selectively binds to a kinase domain dimer interface amino acid residue. In some embodiments, a compound disclosed herein selectively binds to a kinase domain dimer interface amino acid residue, such as one or more of amino acid residues 569-701, 569, 591, 592, 594, 617, 620, 627, 628, 631, 674, 678, or 701 of SEQ ID NO: 1.

In some embodiments, a compound disclosed herein selectively binds to a first IRE1a and blocks dimerization between kinase domain dimer interface amino acid residues of the first IRE1a and a second IRE1a. In some embodiments, a compound disclosed herein selectively binds to a first IRE1a, and inhibit dimerization at one or more of amino acid residues 569-701, 569, 591, 592, 594, 617, 620, 627, 628, 631, 674, 678, or 701 of SEQ ID NO: 1.

In some embodiments, a compound disclosed herein selectively binds to a kinase-extension nuclease (KEN) domain dimer interface amino acid residue of an IRE1a. In some embodiments, a compound disclosed herein selectively binds to a KEN domain dimer interface amino acid residue, such as one or more of amino acid residues 840-925, 840, 844, 851, 908, 912, or 925 of SEQ ID NO: 1.

In some embodiments, a compound disclosed herein selectively binds to amino acid residues of a nuclease active site. In some embodiments, a compound disclosed herein selectively binds to amino acid residues of a nuclease active site, such as one or more of amino acid residues 847-910, 847, 850, 886, 888, 889, 890, 892, 902, 905, 906, or 910 of SEQ ID NO: 1.

In some embodiments, a compound disclosed herein selectively binds to an RNase domain and a trans-autophosphorylation kinase domain region of IRE1a. In some embodiments, a compound disclosed herein selectively binds to an RNase domain and an ATP-binding pocket within a trans-autophosphorylation kinase domain region of IRE1a. In some embodiments, a compound disclosed herein selectively binds to an RNase domain and an activation loop within a trans autophosphorylation kinase domain region of IRE1a.

In some embodiments, a compound disclosed herein selectively binds to IRE1a at two sites located in an RNase domain, trans-autophosphorylation kinase domain region, ATP-binding pocket, activation loop, or any combination thereof. In some embodiments, a compound disclosed herein selectively binds to IRE1a at two or more sites. In some embodiments, a compound disclosed herein selectively binds to IRE1a at two or more sites located in an RNase domain, trans-autophosphorylation kinase domain region, ATP-binding pocket, activation loop, or any combination thereof. In some embodiments, a compound disclosed herein selectively binds to IRE1a at three sites located in an RNase domain, trans-autophosphorylation kinase domain region, ATP-binding pocket, activation loop, or any combination thereof.

In some embodiments, a compound disclosed herein selectively binds to IRE1a at a first site located in an RNase domain, trans-autophosphorylation kinase domain region, ATP-binding pocket, or activation loop. In some embodiments, a first site comprises one or more of any amino acid residue within amino acid residues 465-977 of SEQ ID NO: 1. In some embodiments, a compound disclosed herein selectively binds to IRE1a at a second site located in an RNase domain, trans-autophosphorylation kinase domain region, ATP-binding pocket, or activation loop. In some examples, the first site is located within the same domain or region as the second site. In some examples, the first site is located within a different domain or region as the second site.

In some embodiments, a compound disclosed herein selectively binds to first IRE1a, thereby blocking dimerization of the first IRE1a to a second IRE1a. In some embodiments, a compound disclosed herein selectively binds to first IRE1a, thereby blocking auto-transphosphorylation of the first IRE1a or a second IRE1a to which the first IRE1a is dimerized. In some embodiments, a compound disclosed herein selectively binds to a first IRE1a, thereby blocking activation of the first IRE1a or a second IRE1a to which the first IRE1a is dimerized. In some embodiments, a compound disclosed herein selectively binds to a first IRE1a, thereby blocking kinase activity of the first IRE1a or a second IRE1a to which the first IRE1a is dimerized. In some embodiments, a compound disclosed herein selectively binds to a first IRE1a, thereby blocking RNase activity of the first IRE1a or a second IRE1a to which the first IRE1a is dimerized.

In some embodiments, a compound disclosed herein selectively binds to IRE1a when in a homo-dimerized conformation. In some embodiments, a compound disclosed herein selectively binds to IRE1a when in an oligomerized conformation. In some embodiments, a compound disclosed herein selectively binds to IRE1a when in a non-oligomerized or non-dimerized dimerized conformation. In some embodiments, a compound disclosed herein selectively binds to IRE1a when in an ATP-bound state. In some embodiments, a compound disclosed herein selectively binds to an IRE1 family protein when in a non-ATP-bound state. In some embodiments, the compound is a pharmaceutically acceptable salt, or solvate thereof.

IRE1 Signaling Pathway

In some embodiments, a compound disclosed herein selectively binds to an IRE1 family protein and alters a downstream signaling pathway. In some embodiments, a compound disclosed herein selectively binds to an IRE1 family protein and alters signaling of immunoglobulin heavy-chain binding protein (BIP), protein kinase R (PKR)-like endoplasmic reticulum kinase (PERK), glucose regulate protein 78 (Grp78), eukaryotic translation initiation factor 2α (eIF2α), X-box binding protein 1 (XBP1), activating transcription factor 6a (ATF6a), C/EBP homologous protein (CHOP), growth arrest and DNA damage-inducible protein 34 (GADD34), tumor necrosis factor receptor-associated factor 2 (TRAF2), JUN N-terminal kinase (JNK), regulated IRE1-dependent decay (RIDD), transcriptionally active XBP1 (XBP1s), or unspliced XBP1 (XBP1u). In some embodiments, a compound disclosed herein selectively binds to an IRE1 family protein and alters a downstream cellular process. In some embodiments, an IRE1 family protein is IRE1, IRE1a, or ERN1.

In some embodiments, a compound disclosed herein selectively binds to an IRE1 family protein and decreases or blocks a downstream signaling pathway. In some embodiments, a compound disclosed herein selectively binds to an IRE1 family protein and decreases or blocks activity or signaling of TXNIP, Caspase 1, Interleukin 1-beta, JNK, Bim, cytochrome C, Caspase 3, Caspase 8, mRNA degradation, miRNA degradation, apoptosis-inducing proteins, or inflammation-inducing proteins. In some embodiments, a compound disclosed herein selectively binds to an IRE1 family protein and decreases XBP1 mRNA levels. In some embodiments, a compound disclosed herein selectively binds to an IRE1 family protein and decreases transcriptionally active XBP1 (XBP1s) mRNA levels. In some embodiments, a compound disclosed herein selectively binds to an IRE1 family protein and decreases spliced XBP1 mRNA levels. In some embodiments, an IRE1 family protein is IRE1, IRE1a, or ERN1.

In some embodiments, a compound disclosed herein selectively binds to an IRE1 family protein and increases, activates, or removes a block of a downstream signaling pathway. In some embodiments, a compound disclosed herein selectively binds to an IRE1 family protein and increases, activates, or removes a block of activity or signaling of Bcl2, Bcl-XL, Mcl-1, Bax, Bak, other anti-apoptotic proteins, or an mRNA translocon proteins. In some embodiments, an IRE1 family protein is IRE1, IRE1a, or ERN1.

In some embodiments, a compound disclosed herein selectively binds to an IRE1 family protein and disrupts binding with an effector protein. In some cases, the effector protein binds to the IRE1 family protein when in a dimerized or oligomerized state. In some cases, the effector protein binds to the IRE1 family protein when in a non-dimerized or non-oligomerized state. In some cases, the effector protein is immunoglobulin heavy-chain binding protein (BIP), protein kinase R (PKR)-like endoplasmic reticulum kinase (PERK), glucose regulate protein 78 (Grp78), tumor necrosis factor receptor-associated factor 2 (TRAF2), JUN N-terminal kinase (JNK), transcriptionally active XBP1 (XBP1s), unspliced XBP1 (XBP1u), regulated IRE1-dependent decay (RIDD), Heat shock protein 90 kDa alpha (HSP 90-alpha), or misfolded protein. In some embodiments, an IRE1 family protein is IRE1, IRE1a, or ERN1.

In some embodiments, a compound disclosed herein selectively binds to an IRE1 family protein and alters activity of a cellular process or cellular function, such as regulated IRE1-dependent decay (RIDD), RNA decay, translation, autophagy, cell survival, ER protein folding, ERAD, reactive oxygen species generation, transport, ER-associated protein degradation (ERAD), protein synthesis, or apoptosis. In some embodiments, where an altered or lack of a cellular process or cellular function is associate with a disease state, selective binding of a compound disclosed herein results in inhibiting or alleviating the disease state, or inhibiting a deleterious activity associated with the disease state. In some embodiments, an IRE1 family protein is IRE1, IRE1a, or ERN1.

Diseases Associated with Altered IRE1 Pathway Signaling

In some cases, a compound disclosed herein is used to treat or ameliorate a disease associated with altered IRE1a pathway signaling when administered to a subject in need thereof. In some cases, a compound disclosed herein is used to treat or ameliorate the effects of a disease associated with altered IRE1a pathway signaling when administered to a subject in need thereof. Exemplary disease associated with altered IRE1a signaling include cancer. In some cases, a compound disclosed herein is used to treat or ameliorate a cancer when administered to a subject in need thereof. Exemplary cancers include tumors, solid and hematologic cancers. In some cases, a compound disclosed herein is used to treat or ameliorate a cell proliferative disorder when administered to a subject in need thereof. In some cases, the cell proliferative disorder is a cancer. In some cases, the solid cancer is ovarian cancer, lung cancer, breast cancer, bladder cancer, or triple negative breast cancer (TNBC). In some cases, the hematological cancer is a leukemia, lymphoma, and multiple myeloma.

An IRE1a pathway can be involved in a variety of pathological conditions, including neurodegenerative diseases, inflammation, metabolic disorders, liver dysfunction, brain ischemia, heart ischemia, autoimmune diseases, and cancer. In some cases, modulation of this pathway provides therapeutic methods useful for treatment of such diseases.

In some instances, a compound disclosed herein is used to reinforce anti-tumor mechanisms. In some cases, an anti-tumor mechanism comprises direct inhibition of tumor growth. In some cases, an anti-tumor mechanism comprises induction of anti-tumor immunity. In some cases, anti-tumor mechanisms comprise direct inhibition of tumor growth and simultaneous induction of anti-tumor immunity. In some cases, a compound disclosed herein can prevent lipid accumulation in myeloid cells exposed to ovarian cancer-derived ascites supernatants. In some cases, a compound disclosed herein can block myeloid cell immunosuppression mediated by tumor-associated factors. In some cases, a compound disclosed herein can be employed as therapeutic compound that enhances dendritic cell and T cell anti-tumor activity in mammals. For example, the compounds disclosed herein can be used to treat murine and human ovarian cancers.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of any one of the compounds disclosed. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (e.g., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%), 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg to 5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 mg/kg to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the ED50 with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day, e.g., two, three, four or more times daily.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In one embodiment, the therapeutic effectiveness of one of the compounds described herein is enhanced by administration of an adjuvant {i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

EXAMPLES

Example 1: Synthesis of 5-bromo-3-ethyl-2-fluorobenzaldehyde (1A-4)

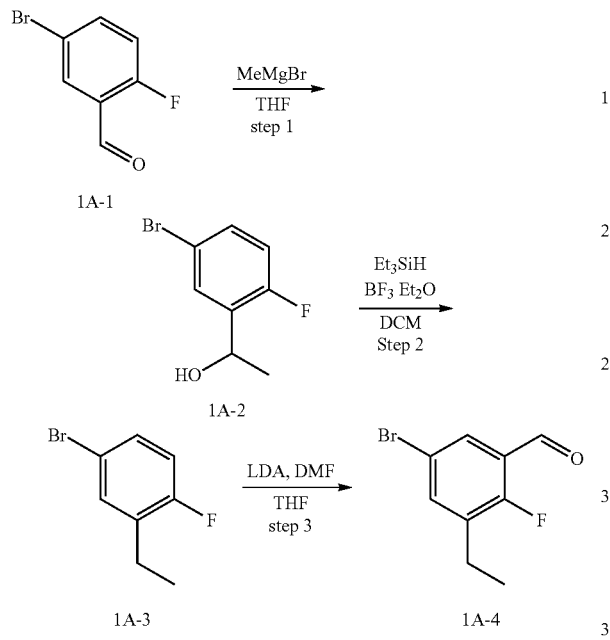

Step 1: 1-(5-Bromo-2-fluorophenyl)ethan-1-ol (1A-2)

A solution of 5-bromo-2-fluoro-benzaldehyde (55.0 g, 270.9 mmol) in THF (500.0 mL) was cooled to 0° C. Then MeMgBr (3 M, 94.8 mL) was added. The mixture was stirred at 0° C. for 0.5 h, quenched with NH$_4$Cl (500 mL) and extracted with ethyl acetate (500 mL×3). The combined organic layers were washed with brine (500 mL×3), dried over Na$_2$SO$_4$, filtered, and concentrated under reduced pressure to give a residue. The residue was purified by column chromatography (SiO$_2$) to afford compound 1A-2 (46.0 g, crude).

Step 2: 4-Bromo-2-ethyl-1-fluorobenzene (1A-3)

To a solution of compound 1A-2 (46.0 g, 210.0 mmol) and triethylsilane (48.8 g, 420.0 mmol, 66.9 mL) in DCM (500.0 mL) was added BF$_3$·Et$_2$O (59.6 g, 420.0 mmol, 51.8 mL) at 0° C. The mixture was stirred at 25° C. for 2 h, concentrated, quenched by addition of sat. NaHCO$_3$ (200 mL) at 0° C., and extracted with ethyl acetate (200 mL×3). The combined organic layers were washed with brine (200 mL×3), dried over Na$_2$SO$_4$, filtered, and concentrated. The residue was purified by column chromatography (SiO$_2$) to afford compound 1A-3 (24.0 g, crude). $^1$H NMR (CHLOROFORM-d, 400 MHz) δ 7.31 (dd, J=2.2, 6.6 Hz, 1H), 7.27-7.21 (m, 1H), 6.87 (t, J=9.2 Hz, 1H), 2.62 (q, J=7.5 Hz, 2H), 1.20 (t, J=7.6 Hz, 3H).

Step 3: 5-Bromo-3-ethyl-2-fluorobenzaldehyde (1A-4)

To a solution of compound 1A-3 (24.0 g, 82.7 mmol) in THF (500 mL) was added LDA (2 M, 49.6 mL) at −78° C. The mixture was stirred at −78° C. for 1 h. Then dimethyl formamide (7.8 g, 107.5 mmol, 8.3 mL) was added and stirred for 1 h at −78° C. The reaction mixture was quenched by addition of NH$_4$Cl (100 mL) and the resulting mixture was extracted with ethyl acetate (200 mL×3). The combined organic layers were washed with brine (100 mL×3), dried over Na$_2$SO$_4$, filtered and concentrated under reduced pressure to give a residue. The residue was purified by column chromatography (SiO$_2$) to afford compound 1A-4 (13.0 g, crude). $^1$H NMR (CDCl$_3$, 400 MHz) δ 10.30 (s, 1H), 7.81 (dd, J=2.6, 5.7 Hz, 1H), 7.58 (dd, J=2.6, 6.4 Hz, 1H), 2.73 (q, J=7.6 Hz, 2H), 1.30-1.25 (m, 3H).

Example 2: Synthesis of 8-ethyl-2-fluoro-6-(4,4,5,5-tetramethyl-1,3,2-dioxaborolan-2-yl)quinazoline (2A-3)

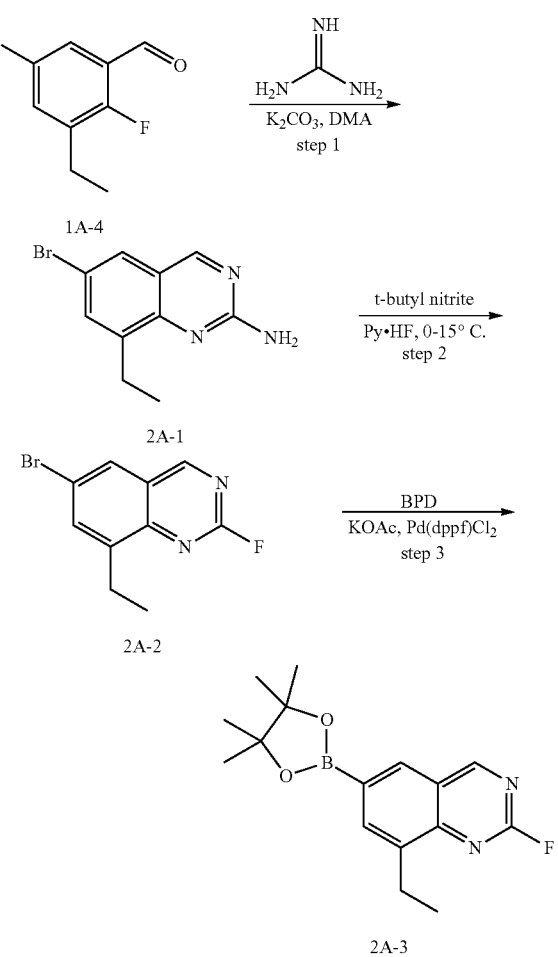

Step 1: 6-Bromo-8-ethylquinazolin-2-amine (2A-1)

To a solution of guanidine (1.7 g, 13.8 mmol, H$_2$CO$_3$) and K$_2$CO$_3$ (5.7 g, 41.4 mmol) in DMA (60.0 mL) was dropwise added 5-bromo-3-ethyl-2-fluorobenzaldehyde (3.0 g, 13.8 mmol) in DMA (9.0 ml). The mixture was stirred at 160° C. for 1 h. The reaction mixture was concentrated under reduced pressure to give a residue. The residue was purified by column chromatography (SiO$_2$) to give 6-bromo-8-ethylquinazolin-2-amine (1.4 g, 24.7% yield). M+H$^+$=257.8 (LCMS).

Step 2: 6-Bromo-8-ethyl-2-fluoroquinazoline (2A-2)

To a solution of 6-bromo-8-ethylquinazolin-2-amine (10 g, 39.6 mmol) in pyridine (100.0 mL) was added pyridine hydrofluoride (220.0 g, 2.2 mol, 200.0 mL) at −40° C. The mixture was stirred at −40° C. for 15 min. Then tert-butyl nitrite (8.2 g, 79.3 mmol, 9.4 mL) was added. The mixture was stirred at 20° C. for 12 h. The mixture was poured into ice water and adjusted pH=7 with sat. NaHCO$_3$, extracted with ethyl acetate (500.0 mL×3). The combined organic layers were washed with brine (200.0 mL×3), dried over Na$_2$SO$_4$, filtered, and concentrated under reduced pressure to give a residue. The residue was purified by column chromatography (SiO$_2$) to afford 6-bromo-8-ethyl-2-fluoroquinazoline (11.4 g, 55.4% yield). M+H$^+$=257.0 (LCMS);

$^1$H NMR (400 MHz, CHLOROFORM-d) δ 9.26 (d, J=2.6 Hz, 1H), 8.00 (d, J=2.2 Hz, 1H), 7.87 (d, J=1.1 Hz, 1H), 3.18 (q, J=7.5 Hz, 2H), 1.37 (t, J=7.5 Hz, 3H).

Step 3: 8-Ethyl-2-fluoro-6-(4,4,5,5-tetramethyl-1,3,2-dioxaborolan-2-yl)quinazoline (2A-3)

To a solution of 6-bromo-8-ethyl-2-fluoroquinazoline (6.0 g, 23.5 mmol) and KOAc (3.5 g, 35.3 mmol) in dioxane (100.0 mL) were added 4,4,4',4',5,5,5',5'-octamethyl-2,2'-bi(1,3,2-dioxaborolane) (7.2 g, 28.2 mmol) and Pd(dppf)Cl$_2$ (1.7 g, 2.3 mmol). The mixture was stirred at 90° for 12 h under N$_2$. The mixture was concentrated to give a residue. The residue was purified by column chromatography (SiO$_2$) to give 8-ethyl-2-fluoro-6-(4,4,5,5-tetramethyl-1,3,2-dioxaborolan-2-yl)quinazoline (7.1 g, 99.9% yield).

Example 3: Synthesis 4-chloro-N-(5-(2-(((1r,4r)-4-(dimethylamino)cyclohexyl)amino)-8-ethylquinazolin-6-yl)-6-methylpyridin-2-yl)pyridine-3-sulfonamide (1)

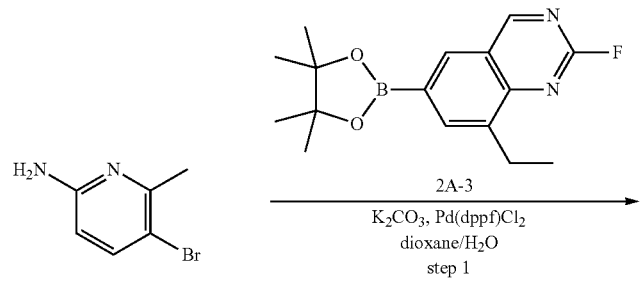

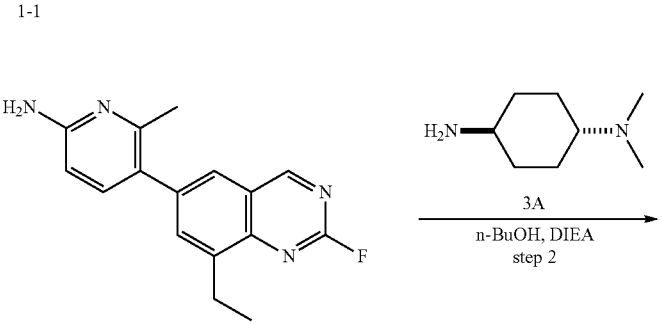

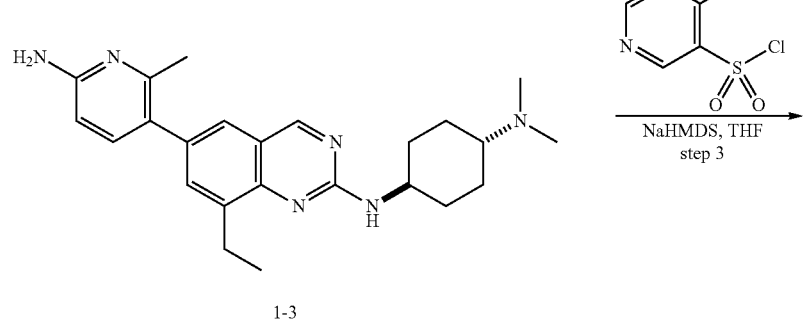

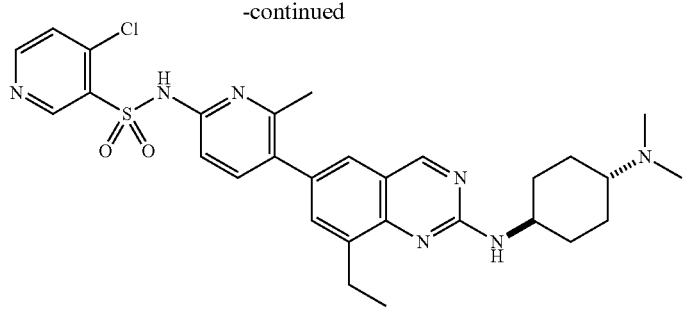

Step 1: 5-(8-Ethyl-2-fluoroquinazolin-6-yl)-6-methylpyridin-2-amine (1-2)

A mixture of compound 2A-3 (1 g, 3.3 mmol), 5-bromo-6-methyl-pyridin-2-amine (742 mg, 3.9 mmol), K₂CO₃ (1.3 g, 9.9 mmol), Pd(dppf)Cl₂ (242 mg, 330.9 umol) in dioxane (20.0 mL) H₂O (2.0 mL) was degassed and purged with N₂ for 3 times, and then the mixture was stirred at 90° C. for 12 h under N₂ atmosphere. The reaction mixture was concentrated under reduced pressure to give a residue. The residue was purified by flash silica gel chromatography to afford compound 1-2 (0.9 g, 2.5 mmol) as a yellow solid. M+H⁺ =282.9.

Step 2: (1r,4r)-N1-(6-(6-amino-2-methylpyridin-3-yl)-8-ethylquinazolin-2-yl)-N4,N4-dimethylcyclohexane-1,4-diamine (1-3)

To a solution of compound 1-2 (0.9 g, 3.1 mmol) in n-BuOH (10.0 mL) was added DIEA (2.0 g, 15.9 mmol, 2.7 mL) and compound 3A (907 mg, 6.3 mmol, HCl). The mixture was stirred at 100° C. for 12 h. The reaction mixture was concentrated under reduced pressure to give a residue. The residue was purified by prep-HPLC (FA condition) to afford compound 1-3 (774 mg, 53.9% yield, formic acid salt (FA)) as a yellow solid. ¹H NMR (400 MHz, METHANOL-d₄) δ 8.97 (s, 1H), 8.38 (s, 1H), 7.57 (d, J=8.6 Hz, 1H), 7.49 (d, J=1.8 Hz, 2H), 6.65 (d, J=8.8 Hz, 1H), 3.96 (tt, J=3.9, 11.5 Hz, 1H), 3.41-3.15 (m, 1H), 3.12-2.99 (m, 2H), 2.92-2.74 (m, 6H), 2.51-2.27 (m, 5H), 2.16 (br d, J=11.9 Hz, 2H), 1.78-1.61 (m, 2H), 1.56-1.38 (m, 2H), 1.30 (t, J=7.5 Hz, 3H). The residue was purified by prep-HPLC (basic condition) to afford compound 1-3 (250 mg, 602.2 umol, 67.8% yield) as a yellow solid. M+H⁺=405.5 (LCMS).

Step 3: 4-Chloro-N-(5-(2-(((1r,4r)-4-(dimethylamino)cyclohexyl)amino)-8-ethylquinazolin-6-yl)-6-methylpyridin-2-yl)pyridine-3-sulfonamide (1)

To a solution of compound 1-3 (230 mg, 568.5 umol) in THF (46.0 mL) was added NaHMDS (1 M, 2.3 mL) at 0° C. The mixture was stirred at 0° C. for 1 h and then 4-chloropyridine-3-sulfonyl chloride (361 mg, 1.7 mmol) was added. The mixture was stirred at 25° C. for 1 h. The reaction mixture was quenched by addition saturated NH₄Cl (10.0 mL), filtered, and concentrated under reduced pressure to give a residue. The residue was purified by prep-HPLC (FA condition) to afford compound 1 (35.6 mg, 9.7% yield, FA) as a yellow solid. M+H⁺=580.3 (LCMS); ¹H NMR (400 MHz, METHANOL-d4) δ 9.24 (s, 1H), 9.00 (s, 1H), 8.61 (d, J=5.3 Hz, 1H), 8.54 (br s, 1H), 7.76 (d, J=9.0 Hz, 1H), 7.64 (d, J=5.3 Hz, 1H), 7.53 (dd, J=1.9, 10.9 Hz, 2H), 7.32 (d, J=8.8 Hz, 1H), 4.06-3.89 (m, 1H), 3.26-3.16 (m, 1H), 3.08 (q, J=7.5 Hz, 2H), 2.85 (s, 6H), 2.47-2.31 (m, 5H), 2.18 (br d, J=12.3 Hz, 2H), 1.80-1.63 (m, 2H), 1.59-1.41 (m, 2H), 1.32 (t, J=7.5 Hz, 3H).

Example 4: Synthesis of 2-chloro-N-(6-methyl-5-(4,4,5,5-tetramethyl-1,3,2-dioxaborolan-2-yl)pyridin-2-yl)benzenesulfonamide (5A-2)

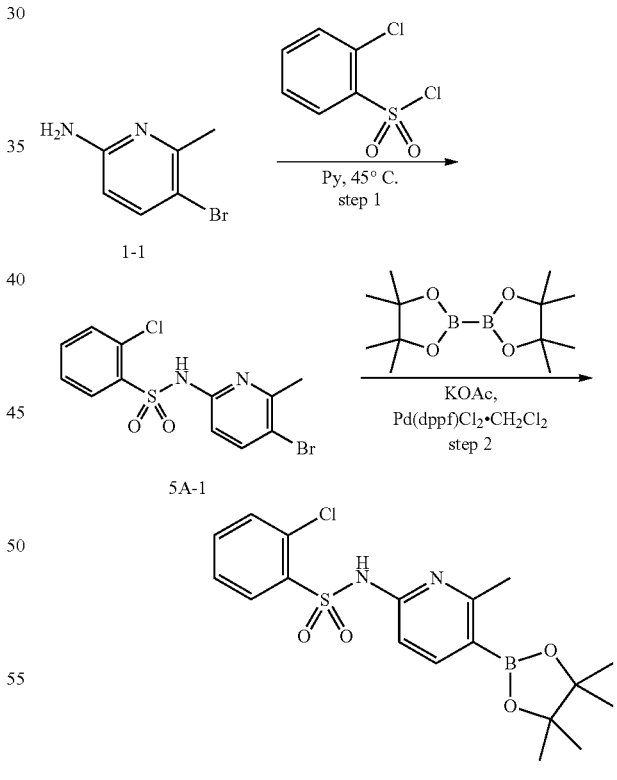

Step 1: N-(5-bromo-6-methylpyridin-2-yl)-2-chlorobenzenesulfonamide (5A-1)

To a solution of 5-bromo-6-methyl-pyridin-2-amine (5.0 g, 26.7 mmol) in pyridine (100.0 mL) was added 2-chlorobenzenesulfonyl chloride (6.7 g, 32.0 mmol, 4.3 mL). The mixture was stirred at 45° C. for 12 h. The reaction mixture was concentrated under reduced pressure to give a residue. The residue was purified by flash silica gel chromatography to afford compound 5A-1 (9.4 g, 82.9% yield) as a pale yellow solid. $^1$H NMR (400 MHz, CHLOROFORM-d) δ 8.24 (br s, 1H), 8.20-8.14 (m, 1H), 7.68-7.60 (m, 1H), 7.53-7.47 (m, 2H), 7.44-7.37 (m, 1H), 6.97 (d, J=8.7 Hz, 1H), 2.50-2.46 (m, 3H).

Step 2: 2-Chloro-N-(6-methyl-5-(4,4,5,5-tetramethyl-1,3,2-dioxaborolan-2-yl)pyridin-2-yl)benzenesulfonamide (5A-2)

A mixture of compound 5A-1 (3 g, 8.3 mmol), 4,4,4',4',5,5,5',5'-octamethyl-2,2'-bi(1,3,2-dioxaborolane) (4.2 g, 16.5 mmol), KOAc (2.4 g, 24.8 mmol), Pd(dppf)Cl$_2$·CH$_2$Cl$_2$ (677 mg, 829.5 umol) in dioxane (60.0 mL) was degassed and purged with N$_2$ for 3 times, and then the mixture was stirred at 110° C. for 12 h under N$_2$ atmosphere. The reaction mixture was concentrated under reduced pressure. The residue was purified by column chromatography (SiO$_2$) to give compound 5A-2 (1 g, 21.5% yield) as a pale yellow oil. M+H$^+$=409.2 (LCMS).

Example 5: Synthesis of 2-chloro-N-(5-(2-(((1r,4r)-4-(dimethylamino)cyclohexyl)amino)-8-ethylpyrido[3,2-d]pyrimidin-6-yl)-6-methylpyridin-2-yl)benzenesulfonamide (2)

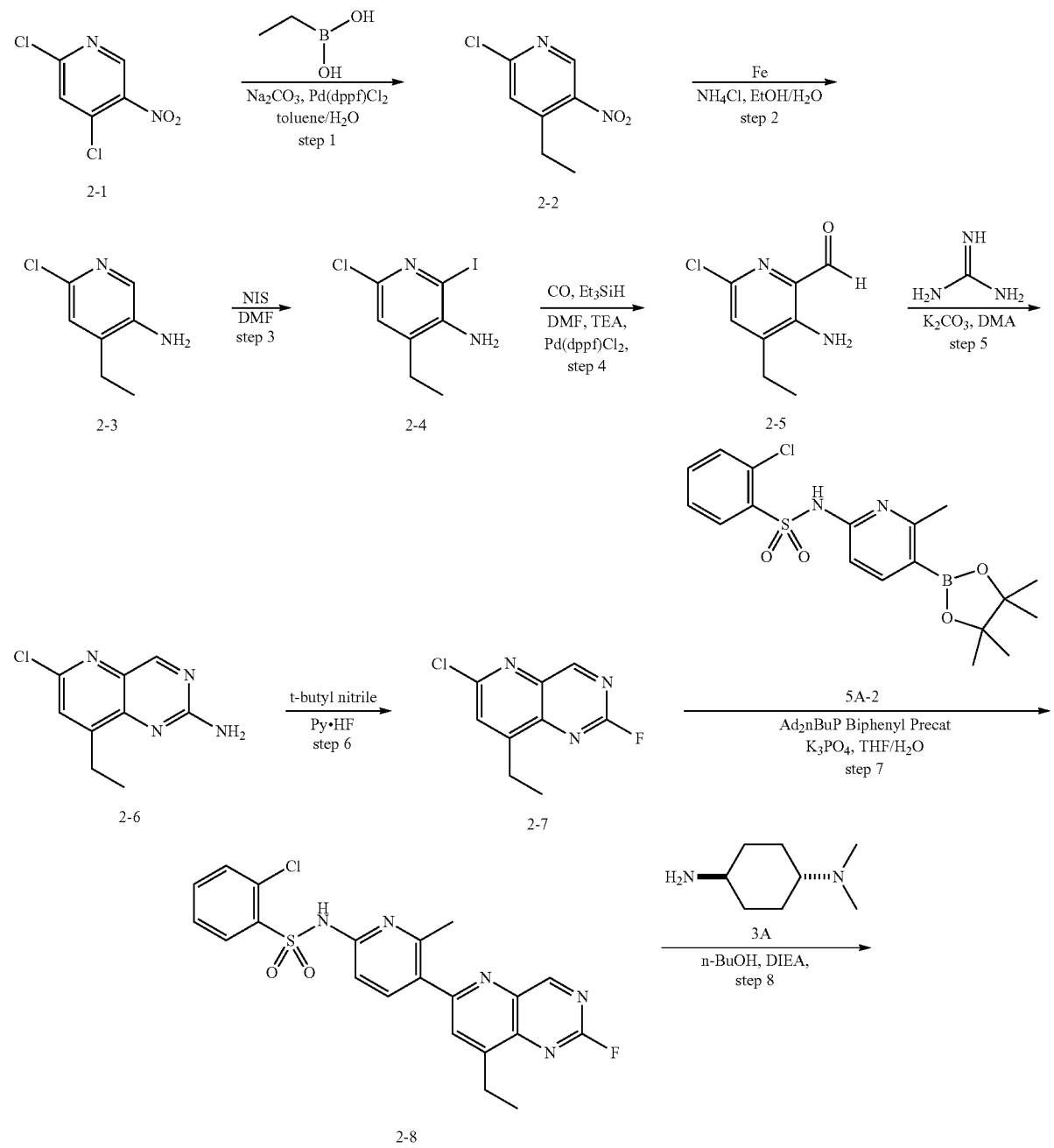

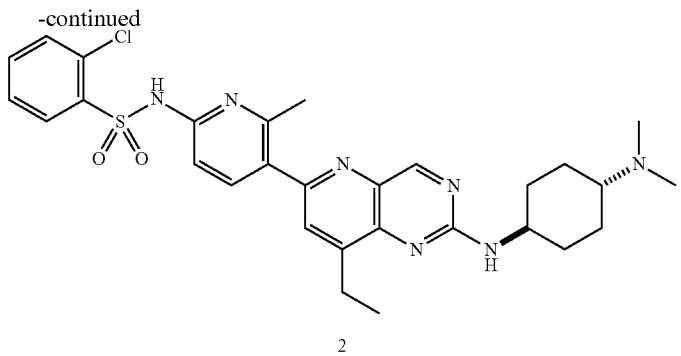

Step 1: 2-Chloro-4-ethyl-5-nitropyridine (2-2)

To a solution of compound 2-1 (10.0 g, 51.8 mmol) and Na$_2$CO$_3$ (6.5 g, 62.1 mmol) in toluene (100.0 mL) and H$_2$O (40.0 mL) were added ethylboronic acid (4.2 g, 57.0 mmol) and Pd(dppf)Cl$_2$ (1.9 g, 2.5 mmol). The mixture was stirred at 90° C. for 12 h under N$_2$. The mixture was concentrated to give a residue. The residue was purified by flash silica gel chromatography to give compound 2-2 (6.8 g, 70.3% yield) as a colorless oil. $^1$H NMR (400 MHz, CHLOROFORM-d) δ 8.95 (s, 1H), 7.38 (s, 1H), 3.00 (q, J=7.5 Hz, 2H), 1.34 (t, J=7.5 Hz, 3H).

Step 2: 6-Chloro-4-ethylpyridin-3-amine (2-3)

To a solution of compound 2-2 (5.7 g, 30.5 mmol) in EtOH (60.0 mL) and H$_2$O (12.0 mL) was added Fe (5.1 g, 91.6 mmol) and NH$_4$Cl (8.1 g, 152.7 mmol). The mixture was stirred at 80° C. for 12 h. The reaction mixture was filtrated by diatomite to remove the undissolved substance and washed by methanol (50.0 mL×3). The filtrate was concentrated under reduced pressure. The residue was diluted with water (100.0 mL) and extracted with ethyl acetate (50.0 mL×3). The combined organic layers were washed with saturated sodium chloride (50.0 mL×2), dried over anhydrous sodium sulfate, filtered, and concentrated under reduced pressure to give a residue. The residue was purified by flash silica gel chromatography to afford compound 2-3 (3.6 g, 23.1 mmol, 75.6% yield) as a yellow oil.

Step 3: 6-Chloro-4-ethyl-2-iodopyridin-3-amine (2-4)

To a solution of compound 2-3 (3.6 g, 23.1 mmol) in DMF (35.0 mL) was added NIS (5.2 g, 23.1 mmol). The mixture was stirred at 25° C. for 6 h. The reaction mixture was diluted with water (150.0 mL) and extracted with ethyl acetate (100.0 mL×3). The combined organic layers were dried over anhydrous sodium sulfate, filtered, and concentrated under reduced pressure to give a residue. The residue was purified by flash silica gel chromatography to afford compound 2-4 (3.0 g, 10.6 mmol, 45.8% yield) as a brown solid.

Step 4: 3-Amino-6-chloro-4-ethylpicolinaldehyde (2-5)

To a solution of compound 2-4 (3.5 g, 12.5 mmol) in DMF (150.0 mL) was added Et$_3$SiH (2.9 g, 25.1 mmol, 4.0 mL), TEA (3.8 g, 37.7 mmol, 5.2 mL) and Pd(dppf)Cl$_2$ (919 mg, 1.2 mmol) under N$_2$. The suspension was degassed under vacuum and purged with CO several times. The mixture was stirred under CO (50 psi) at 50° C. for 12 h. The reaction mixture was diluted with water (100.0 mL) and extracted with ethyl acetate (50.0 mL×3). The combined organic layers were washed with saturated sodium chloride (50.0 mL×2), dried over anhydrous sodium sulfate, filtered, and concentrated under reduced pressure to give a residue. The residue was purified by column chromatography (SiO$_2$) to give compound 2-5 (1.5 g, 64.6% yield) as a yellow solid. $^1$H NMR (400 MHz, CHLOROFORM-d) δ 9.99 (s, 1H), 7.16 (s, 1H), 6.26 (br s, 2H), 2.53 (dq, J=0.8, 7.5 Hz, 2H), 1.32 (t, J=7.4 Hz, 3H).

Step 5: 6-Chloro-8-ethylpyrido[3,2-d]pyrimidin-2-amine (2-6)

To a solution of guanidine (262 mg, 2.1 mmol, H$_2$CO$_3$) and K$_2$CO$_3$ (449 mg, 3.2 mmol) in DMA (2.5 mL) was dropwise added compound 2-5 (200 mg, 1.0 mmol) in DMA (2.5 mL). The mixture was stirred at 160° C. for 1 h. The reaction mixture was diluted with water (10.0 mL) and extracted with ethyl acetate (10.0 mL×3). The combined organic layers were washed with saturated sodium chloride (10.0 mL×2), dried over anhydrous sodium sulfate, filtered, and concentrated to 2.0 mL under reduced pressure. The mixture was filtered and the filter cake was washed with ethyl acetate (1.0 mL) to give compound 2-6 (84 mg, crude) as a yellow solid. $^1$H NMR (400 MHz, DMSO-d$_6$) δ 9.03 (s, 1H), 7.56 (s, 1H), 7.22 (s, 2H), 3.01-2.90 (m, 2H), 1.25 (t, J=7.5 Hz, 3H).

Step 6: 6-Chloro-8-ethyl-2-fluoropyrido[3,2-d]pyrimidine (2-7)

To a solution of compound 2-6 (84 mg, 402.5 umol) in pyridine (2 mL) was added pyridine hydrofluoride (2.4 g, 16.9 mmol, 2.1 mL, 70% purity) at −40° C. The mixture was stirred at −40° C. for 15 min. Then tert-butyl nitrite (83 mg, 805.1 umol, 95.7 uL) was added. The mixture was stirred at 25° C. for 1 h. The reaction mixture was quenched by addition saturated NaHCO$_3$ (50.0 mL) and extracted with EtOAc (30.0 mL×3). The combined organic layers were washed with brine (30.0 mL×3), dried over Na$_2$SO$_4$, filtered, and concentrated under reduced pressure to give a residue. The residue was purified by column chromatography (SiO$_2$) to give compound 2-7 (47 mg, 49.6% yield) as a yellow solid. $^1$H NMR (400 MHz, CHLOROFORM-d) δ 9.46 (d, J=1.98 Hz, 1H), 7.66 (s, 1H), 3.21 (q, J=7.50 Hz, 2H), 1.41 (t, J=7.61 Hz, 3H).

Step 7: 2-Chloro-N-(5-(8-ethyl-2-fluoropyrido[3,2-d]pyrimidin-6-yl)-6-methylpyridin-2-yl) benzenesulfonamide (2-8)

A mixture of compound 2-7 (47 mg, 222.0 umol), compound 5A-2 (example 5) (90 mg, 222.0 umol), $K_3PO_4$ (0.5 M, 888.3 uL) and [2-(2-aminophenyl)phenyl]-chloro-palladium; bis(1-adamantyl)-butyl-phosphane (14 mg, 22.2 umol) in THF (2.0 mL) was degassed and purged with $N_2$ for 3 times, and then the mixture was stirred at 80° C. for 12 h under $N_2$ atmosphere. The reaction was concentrated to give a residue. The residue was purified by column chromatography ($SiO_2$) to afford compound 2-8 (167 mg, crude) as a yellow oil. $M+H^+=458.0$ (LCMS).

Step 8: 2-Chloro-N-(5-(2-((((1r,4r)-4-(dimethylamino)cyclohexyl)amino)-8-ethylpyrido[3,2-d]pyrimidin-6-yl)-6-methylpyridin-2-yl)benzenesulfonamide (2)

To a solution of compound 2-8 (167 mg, 364.7 umol) in n-BuOH (4.0 mL) was added compound 3A (103 mg, 729.4 umol, HCl) and DIEA (235 mg, 1.8 mmol, 317.6 uL). The mixture was stirred at 100° C. for 12 h. The reaction mixture was concentrated under reduced pressure to give a residue. The residue was purified by prep-HPLC (FA condition) to give compound 2 (12.7 mg, 5.0% yield, FA) as a pale yellow solid. $M+H^+=580.2$ (LCMS); $^1H$ NMR (400 MHz, METHANOL-$d_4$) δ 9.05 (s, 1H), 8.56-8.44 (m, 1H), 8.24 (d, J=7.5 Hz, 1H), 7.87 (d, J=9.0 Hz, 1H), 7.65 (s, 1H), 7.57-7.43 (m, 3H), 7.28-7.17 (m, 1H), 4.08-3.88 (m, 1H), 3.25-3.16 (m, 1H), 3.11 (q, J=7.5 Hz, 2H), 2.86 (s, 6H), 2.48 (s, 3H), 2.41-2.32 (m, 2H), 2.23-2.11 (m, 2H), 1.80-1.66 (m, 2H), 1.57-1.43 (m, 2H), 1.36 (t, J=7.4 Hz, 3H).

Exemplary compounds were synthesized according to procedures described herein. For compounds that do not have a specific synthetic scheme described herein, such compounds can be routinely synthesized by a skilled artisan armed with the guidance presented herein and skill in the art.

II. Biological Evaluation

Example 1: In Vitro FRET Assay

In vitro FRET assay was performed to evaluate the ability of select compounds to inhibit IRE1, the results of which are summarized in Table 3. To perform the in vitro FRET assay, 1× complete assay buffer (CAB; 1M DTT, 50 mM sodium citrate pH 7.15, 1 mM magnesium acetate, 0.02% tween 20) was used to dilute SignalChem IRE1a protein to a final concentration of 2 nM. Selected compounds were serially diluted with DMSO in a non-binding black 384-well plate for a total of 15 ul in each well. 2 ul of the serially diluted compound or DMSO control were then added to new wells containing 98 ul of 1× CAB, for a total volume of 100 ul, 10 ul of which were then transferred to wells of a new plate. 5 ul of the diluted IRE1a was then added to each well. 5 ul of a 400 mM XBP1 RNA probe was then added to each well. Fluorescence was then read over 30 minutes in kinetic mode (485/515 nm).

Two RNA probes were used, XBP1 wildtype (SEQ ID NO: 2) which is able to be spliced by active IRE1a or XBP1 mutant (SEQ ID NO: 3) which is unable to be spliced. Each probe contained a 5' 6-FAM modification and a 3' IOWA Black FQ modification.

A second FRET assay was performed to assess ATP-mediated inhibition. In this case, compounds and IRE1a were prepared and combined as discussed above, with the addition of ATP up to 1 mM final concentration. This mixture was incubated at room temperature for 60 minutes and then 5 ul of 400 nM XBP1 wildtype or mutant RNA probe was added. Plates were then read over 30 minutes in kinetic mode (485/515 nm).

TABLE 3

| Compound Ref. No. | Mean $IC_{50}$ |
| --- | --- |
| 1; Formic Acid Salt | A |
| 2; Formic Acid Salt | A |

Note:
Biochemical assay Mean $IC_{50}$ data are designated within the following range: A: ≤5 nM.

Example 2: In Vitro Luciferase Assay

Compounds disclosed herein were assessed for disruption of IRE1 signaling using a IRE1a Endoribonuclease Nanoluciferase Assay. Briefly, 2.5×10$^6$ 293T cells were seeded in a 10 cm$^2$ tissue culture plate. About 24 hours later, the cells were transfected with Effectene. In a 15 mL tube, the following was added: 2 ug XBP1 luciferase reporter plasmid (PGK-Luc2-P2A-XBP1u-Nanoluciferase-PEST); 300 ul EC buffer; and 16 ul Enhancer, followed by incubation at room temp for 5 minutes. Next, 60 ul Effectene (Qiagen 301427) was added, followed by incubation at room temperature for 10 minutes. 2.6 mL cDMEM media was added. Old media was aspirated from the cells, followed by addition of 7 mL fresh media. Full transfection mixture was added dropwise to cells. Cells were incubated for 6 hours, followed by trypsinization, centrifugation and resuspension in 11 mL fresh cDMEM media. 100 uL of cells were plated per a well in a 96 well plate. A day later, ER stressors of choice +/− inhibitors were added. To harvest, media was aspirated from cells completely, then 50 uL 1× passive lysis buffer (Promega: E1941) was added per well and put on shaker (300 rpm) for 30 minutes at room temperature. Cells were centrifuged, and 15 uL sample per well was added to a new, opaque white 384 well plate (Corning 3570). 15 uL OneGlo (nanoluciferase kit, Promega N1630) was added. Plates were spun down, placed on shaker (300 rpm) for 10 minutes. Plates were read on luminometer, 1000 ms integration time per well. 15 uL Stop and Glo (nanoluciferase kit) was added. Plates were spun down, placed on shaker (300 rpm) for 10 minutes. Plates were read on luminometer, 1000 ms second integration time per well. Recordings are provided below in Table 4.

TABLE 4

| Compound Ref. No. | Mean $EC_{50}$ |
| --- | --- |
| 1; Formic Acid Salt | A |
| 2; Formic Acid Salt | A |

Note:
Biochemical assay Mean $EC_{50}$ data are designated within the following range: A: ≤5 nM.

Example 3: Growth Assay

A growth assay is performed to evaluate the compounds disclosed in Table 1 for cytotoxicity. Briefly, 5,000,000 293T cells are resuspended in 18 mL of cDMEM for a final concentration of 277,777 cells/mL. 180 μL(50,000 cells) cDMEM was seeded per well in 96 well flat bottom plate, with some wells left unfilled. In a 96 well plate, 199 L cDMEM and 1 uL of any one of the compounds disclosed herein. 133.3 uL cDMEM is added to wells 1, 2, 3, 5, 6, 7, 9, 10, and 11 of row A. Wells are serially diluted with 66.7 uL (highest concentration on right, lowest on left) to the total concentrations shown below. 20 uL of each dilution is transferred in duplicate to the cells plated in the 96-well plate. The plate is then placed in a humidified chamber for a 2 day incubation, and then photographed (media is more yellow in wells with potent cell growth). Absorbance is then measured at ~535 nM (lower for more acidic media) and ~450 nM (higher for more acidic media).

Compounds 1 and 2 had percentage growth at 5 uM greater than 90%.

Example 4: Microsome Stability Assay

The formic acid salt of a compound from Table 1 is tested under the microsome stability assay outlined below. Test compounds are incubated at 37° C. with liver microsomes (pooled from multiple donors) at 1 µM in the presence of a NADPH regenerating system at 0.5 mg/ml microsomal protein. Positive controls included Testosterone (3A4 substrate), Propafenone (2D6) and Diclofenac (2C9), which are incubated with microsomes in the presence of an NADPH regenerating system. At time points (0, 5, 10, 20, 30 and 60 minutes), samples are removed and immediately mixed with cold acetonitrile containing internal standard (IS). Test compounds incubated with microsomes without the NADPH regenerating system for 60 min is also included. A single point for each test condition (n=1) is obtained, and samples are analyzed by LC/MS/MS. Disappearance of the test compound is assessed based on peak area ratios of analyte/IS (no standard curve). A number of compounds showed good stability in human and mouse liver microsomes with a T½ of over 40-80 minutes and low microsome clearance. Compound 1 was tested and had 45% or more of parent compound remaining after a 60 minute incubation.

While various embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

SEQUENCE LISTING

SEQ ID NO: 1
MPARRLLLLLTLLLPGLGIFGSTSTVTLPETLLFVSTLDGSLHAVSKRTG
SIKWTLKEDPVLQVPTHVEEPAFLPDPNDGSLYTLGSKNNEGLTKLPFTI
PELVQASPCRSSDGILYMGKKQDIWYVIDLLTGEKQQTLSSAFADSLCPS
TSLLYLGRTEYTITMYDTKTRELRWNATYFDYAASLPEDDVDYKMSHFVS
NGDGLVVTVDSESGDVLWIQNYASPVVAFYVWQREGLRKVMHINVAVETL
RYLTFMSGEVGRITKWKYPFPKETEAKSKLTPTLYVGKYSTSLYASPSMV
HEGVAVVPRGSTLPLLEGPQTDGVTIGDKGECVITPSTDVKFDPGLKSKN
KLNYLRNYWLLIGHHETPLSASTKMLERFPNNLPKHRENVIPADSEKKSF
EEVINLVDQTSENAPTTVSRDVEEKPAHAPARPEAPVDSMLKDMATIILS
TFLLIGWVAFIITYPLSMHQQQQLQHQQFQKELEKIQLLQQQQQQLPFHP
PGDTAQDGELLDTSGPYSESSGTSSPSTSPRASNHSLCSGSSASKAGSSP
SLEQDDGDEETSVVIVGKISFCPKDVLGHGAEGTIVYRGMFDNRDVAVKR
ILPECFSFADREVQLLRESDEHPNVIRYFCTEKDRQFQYIAIELCAATLQ
EYVEQKDFAHLGLEPITLLQQTTSGLAHLHSLNIVHRDLKPHNILISMPN
AHGKIKAMISDFGLCKKLAVGRHSFSRRSGVPGTEGWIAPEMLSEDCKEN
PTYTVDIFSAGCVFYYVISEGSHPFGKSLQRQANILLGACSLDCLHPEKH
EDVIARELIEKMIAMDPQKRPSAKHVLKHPFFWSLEKQLQFFQDVSDRIE
KESLDGPIVKQLERGGRAVVKMDWRENITVPLQTDLRKFRTYKGGSVRDL
LRAMRNKKHHYRELPAEVRETLGSLPDDFVCYFTSRFPHLLAHTYRAMEL
CSHERLFQPYYFHEPPEPQPPVTPDAL

SEQ ID NO: 2
CAUGUCCGCAGCACAUG

SEQ ID NO: 3
CAUGUCCCCAGCACAUG

---

What is claimed is:

1. A compound of Formula (I), or a pharmaceutically acceptable salt, or solvate thereof:

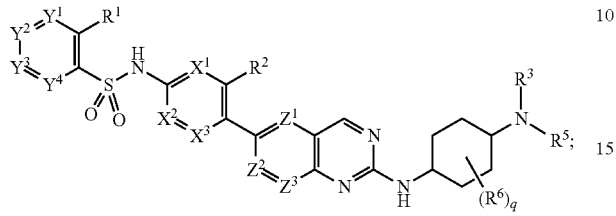

Formula (I)

wherein, $Y^1$, $Y^2$, $Y^3$, and $Y^4$ are each independently selected from N and $CR^8$; $Z^1$ is independently selected from N and $CR^7$; $Z^2$ is independently selected from N and $CR^{7A}$, and $Z^3$ is independently selected from N and $CR^{7B}$; wherein at least one of $Y^1$, $Y^2$, $Y^3$, $Y^4$, $Z^1$, $Z^2$ and $Z^3$ are N and not more than two of $Y^1$, $Y^2$, $Y^3$, and YA are N;

$X^1$, $X^2$, and $X^3$ are each independently selected from N and $CR^4$;

$R^1$ is halogen, —CN, —$OR^{10}$, optionally substituted $C_1$-$C_4$alkyl, optionally substituted $C_1$-$C_4$fluoroalkyl, or optionally substituted $C_1$-$C_4$heteroalkyl;

$R^2$ is hydrogen, —CN, —$OR^{10}$, —$SR^{10}$, optionally substituted $C_1$-$C_4$alkyl, optionally substituted $C_1$-$C_4$fluoroalkyl, optionally substituted —O—$C_1$-$C_4$alkyl, optionally substituted $C_1$-$C_4$heteroalkyl, optionally substituted $C_3$-$C_6$cycloalkyl, optionally substituted —O—$C_3$-$C_6$cycloalkyl, optionally substituted $C_3$-$C_6$heterocycloalkyl, optionally substituted —O—$C_3$-$C_6$heterocycloalkyl, optionally substituted aryl, or optionally substituted heteroaryl;

$R^3$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^4$ is independently H, halogen, —CN, —$OR^{10}$, —$SR^{10}$, —$S(=O)R^9$, —$S(=O)_2R^9$, —$S(=O)_2N(R^{11})_2$, —$NR^{10}S(=O)_2R^3$, —$C(=O)R^9$, —$OC(=O)R^9$, —$C(=O)OR^{10}$, —$OC(=O)OR^9$, —$N(R^{11})_2$, —$OC(=O)N(R^{11})_2$, —$NR^{10}C(=O)R^9$, —$NR^{10}C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^5$ is H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_3$-$C_6$cyclooalkylalkyl, optionally substituted $C_2$-$C_{10}$heterocycloalkyl, optionally substituted aryl, or optionally substituted heteroaryl;

each $R^6$ is independently halogen, —CN, —$OR^{10}$, —$SR^{10}$, —$S(=O)R^9$, —$S(=O)_2R^9$, —$S(=O)_2N(R^{11})_2$, —$NR^{10}S(=O)$; $R^9$, —$C(=O)R^9$, —$OC(=O)R^9$, —$C(=O)OR^{10}$, —$OC(=O)OR^9$, —$N(R^{11})_2$, —$OC(=O)N(R^{11})_2$, —$NR^{10}C(=O)R^9$, —$NR^{10}C(=O)OR^9$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted aryl, or optionally substituted heteroaryl;

$R^7$, $R^{7A}$, and $R^{7B}$ are independently H, —CN, halogen, —$OR^9$, optionally substituted $C_1$-$C_4$alkyl, optionally substituted $C_1$-$C_4$heteroalkyl, optionally substituted $C_1$-$C_4$fluoroalkyl, or optionally substituted aryl;

each $R^8$ is independently H, halogen, —CN, —$OR^{10}$, —$SR^{10}$, —$N(R^{11})_2$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, optionally substituted $C_2$-$C_{10}$heterocycloalkyl, optionally substituted aryl, or optionally substituted heteroaryl;

each R' is independently optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{10}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

each $R^{11}$ is independently H, optionally substituted $C_1$-$C_4$alkyl, optionally substituted $C_1$-$C_4$heteroalkyl, optionally substituted $C_1$-$C_4$fluoroalkyl, optionally substituted $C_3$-$C_6$cycloalkyl, optionally substituted $C_2$-$C_{10}$heterocycloalkyl, optionally substituted aryl, or optionally substituted heteroaryl;

or two $R^1$ are taken together with the N atom to which they are attached to form an optionally substituted heterocycle; and q is 0, 1, 2, 3, or 4.

2. The compound of claim 1 having Formula (Ia), (Ib), (Ic (Id), or a pharmaceutically acceptable salt or solvate thereof:

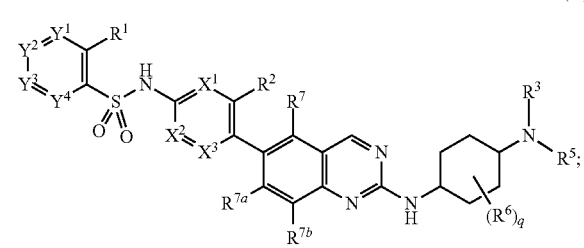

Formula (Ia)

wherein $Y^1$, $Y^2$, $Y^3$, and $Y^4$ are each independently selected from N and $CR^8$, and wherein one or two of $Y^1$, $Y^2$, $Y^3$, and $Y^4$ are N;

Formula (Ib)

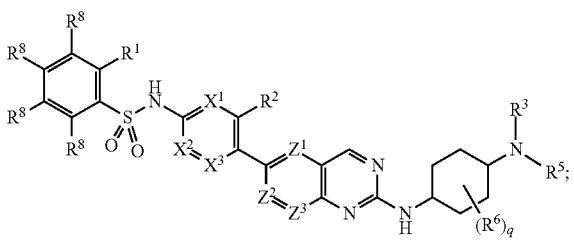

wherein $Z^1$ is independently selected from N and $CR^7$, $Z^2$ is independently selected from N and $CR^{7A}$, and $Z^3$ is independently selected from N and $CR^{7B}$, and wherein at least one of $Z^1$, $Z^2$ and $Z^3$ are N;

Formula (Ic)

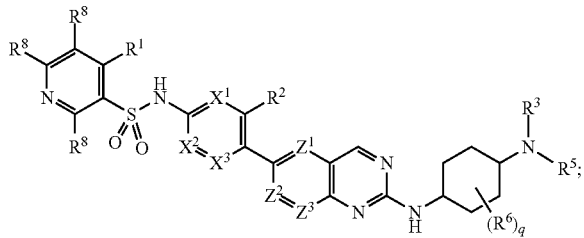

wherein $Z^1$ is independently selected from N and $CR^7$, $Z^2$ is independently selected from N and $CR^{7A}$, and $Z^3$ is independently selected from N and $CR^7B$;

Formula (Id)

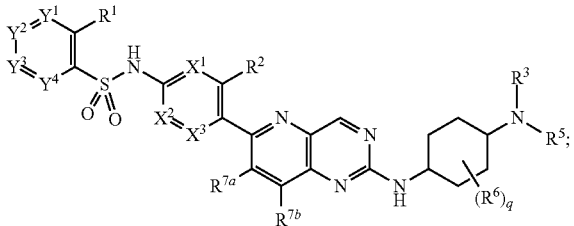

wherein $Y^1$, $Y^2$, $Y^3$, and $Y^4$ are each independently selected from N and $CR^8$, and wherein not more than two of YL, $Y^2$, $Y^3$, and $Y^4$ are N.

3. The compound of claim 1, or a pharmaceutically acceptable salt, or solvate thereof, wherein $Z^1$ is $CR^7$, $Z^2$ is $CR^{7A}$, and $Z^3$ is $CR^7B$.

4. The compound of claim 3, or a pharmaceutically acceptable salt, or solvate thereof, wherein $R^7$ is H.

5. The compound of claim 1, or a pharmaceutically acceptable salt, or solvate thereof, wherein:

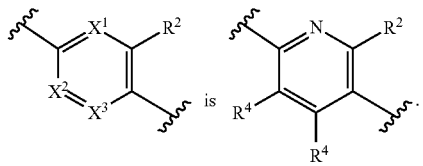

6. The compound of claim 1 wherein each $R^4$ is independently H, halogen, —CN, —$OR^8$, optionally substituted $C_1$-$C_4$alkyl, optionally substituted $C_1$-$C_4$fluoroalkyl, or optionally substituted $C_1$-$C_4$heteroalkyl.

7. The compound of claim 6, or a pharmaceutically acceptable salt, or solvate thereof, wherein each $R^1$ is independently H, fluorine, chlorine, —CN, or unsubstituted $C_1$-$C_4$alkyl.

8. The compound of claim 6, or a pharmaceutically acceptable salt, or solvate thereof, wherein each $R^4$ is H.

9. The compound of claim 1, or a pharmaceutically acceptable salt, or solvate thereof, wherein $R^2$ is —CN, —$OR^{10}$, optionally substituted $C_1$-$C_4$alkyl, optionally substituted $C_1$-$C_4$fluoroalkyl, optionally substituted $C_1$-$C_4$heteroalkyl, optionally substituted $C_3$-$C_6$cycloalkyl, or optionally substituted —O—$C_3$-$C_6$cycloalkyl.

10. The compound of claim 9, or a pharmaceutically acceptable salt, or solvate thereof, wherein $R^2$ is methyl or methoxy.

11. The compound of claim 1, or a pharmaceutically acceptable salt, or solvate thereof, wherein $R^1$ is halogen, —CN, —$OR^8$, optionally substituted $C_1$-$C_4$alkyl, or optionally substituted $C_1$-$C_4$fluoroalkyl.

12. The compound of claim 11 or a pharmaceutically acceptable salt, or solvate thereof, wherein $R^1$ is chlorine.

13. The compound of claim 1, or a pharmaceutically acceptable salt, or solvate thereof, wherein q is zero.

14. The compound of claim 1, or a pharmaceutically acceptable salt, or solvate thereof, wherein $R^3$ is H or optionally substituted $C_1$-$C_4$alkyl.

15. The compound of claim 14, or a pharmaceutically acceptable salt, or solvate thereof, wherein $R^3$ is methyl.

16. The compound of claim 1, or a pharmaceutically acceptable salt, or solvate thereof, wherein $R^5$ is H or optionally substituted $C_1$-$C_4$alkyl.

17. The compound of claim 16, or a pharmaceutically acceptable salt, or solvate thereof, wherein $R^5$ is methyl.

18. The compound of claim 1, or a pharmaceutically acceptable salt or solvate thereof, wherein
$R^1$ is chlorine, fluorine, or unsubstituted $C_1$-$C_4$alkyl;
$R^2$ is unsubstituted $C_1$-$C_4$alkyl or unsubstituted —O—$C_1$-$C_4$alkyl;
$R^3$ is hydrogen or unsubstituted $C_1$-$C_4$alkyl;
each $R^4$ is independently selected from hydrogen, fluorine, chlorine, —CN, or unsubstituted $C_1$-$C_4$alkyl;
$R^5$ is hydrogen or unsubstituted $C_1$-$C_4$alkyl;
each $R^6$ is independently selected from fluorine, —OH, or unsubstituted $C_1$-$C_4$alkyl and q is 0, 1, or 2;
$Z^1$ is N or $CR^7$ wherein $R^7$ is hydrogen, fluorine, chlorine, —CN, or unsubstituted $C_1$-$C_4$alkyl;
$Z^2$ is N or $CR^{7A}$ wherein RA is hydrogen, fluorine, chlorine, —CN, or unsubstituted $C_1$-$C_4$alkyl;
$Z^3$ is N or $CR^{7B}$ wherein $R^{7B}$ is hydrogen, fluorine, chlorine, —CN, or unsubstituted $C_1$-$C_4$alkyl;
$Y^1$ is N or $CR^8$;
$Y^2$ is N or $CR^8$;
$Y^3$ is N or $CR^8$,
$Y^4$ is N or $CR^8$;
each $R^8$ is independently selected from hydrogen, fluorine, chlorine, —CN, and unsubstituted $C_1$-$C_4$alkyl,
$X^1$ is N or $CR^4$;
$X^2$ is N or $CR^4$; and
$X^3$ is N or $CR^4$; wherein at least one of $Y^1$, $Y^2$, $Y^3$, $Y^4$, Z), $Z^2$, and $Z^3$ are N and not more than two of $Y^1$, $Y^2$, $Y^3$, and $Y^4$ are N.

19. The compound of claim 1, or a pharmaceutically acceptable salt, or solvate thereof, wherein $R^1$ is chlorine;
$R^2$ is unsubstituted $C_1$-$C_4$alkyl or unsubstituted —O—$C_1$-$C_4$alkyl;
$R^3$ is hydrogen or unsubstituted $C_1$-$C_4$alkyl;
$R^4$ is hydrogen;
$R^5$ is hydrogen or unsubstituted $C_1$-$C_4$alkyl;
$R^6$ is absent as q is zero;
$Z^1$ is N or $CR^7$ wherein $R^7$ is H;
$Z^2$ is N or $CR^{7A}$ wherein $R^{7A}$ is H;
$Z^3$ is N or $CR^{7B}$ wherein $R^{7B}$ is unsubstituted $C_1$-$C_4$alkyl;
$Y^1$ is N or $CR^8$,
$Y^2$ is N or $CR^8$,
$Y^3$ is N or $CR^8$;
$Y^4$ is N or $CR^8$;
$R^8$ is hydrogen;
$X^1$ is N or $CR^4$;
$X^2$ is N or $CR^4$; and
$X^3$ is N or $CR^4$; wherein at least one of $Y^1$, $Y^2$, $Y^3$, $Y^4$, $Z^1$, $Z^2$, and $Z^3$ are N and not more than two of $Y^1$, $Y^2$, $Y^3$, and $Y^4$ are N.

20. The compound of claim 1, or a pharmaceutically acceptable salt, or solvate thereof, wherein
$R^1$ is chlorine;
$R^2$ is methyl or methoxy;
$R^3$ is hydrogen or methyl;
$R^4$ is hydrogen;
$R^5$ is hydrogen or methyl;
$R^6$ is absent as q is zero;
$Z^1$ is N or $CR^7$ wherein $R^7$ is H;
$Z^2$ is N or $CR^{7A}$ wherein RA is H;
$Z^3$ is N or $CR^{7B}$ wherein $R^{78}$ is ethyl;
$Y^1$ is N or $CR^8$;
$Y^2$ is N or $CR^8$,
$Y^3$ is N or $CR^8$;
$Y^4$ is N or $CR^8$;
$R^8$ is hydrogen;
$X^1$ is N or $CR^4$,
$X^2$ is N or $CR^4$; and
$X^3$ is N or $CR^4$; with the proviso that at least one of $Y^1$, $Y^2$, $Y^3$, YA, $Z^1$, $Z^2$, and $Z^3$ are N and not more than two of $Y^1$, $Y^2$, $Y^3$, and $Y^4$ are N.

21. A compound, or a pharmaceutically acceptable salt or solvate thereof, selected from:
4-chloro-N-(5-(2-(((1r,4r)-4-(dimethylamino)cyclohexyl)amino)-8-ethylquinazolin-6-yl)-6-methylpyridin-2-yl)pyridine-3-sulfonamide; and
2-chloro-N-(5-(2-(((1r,4r)-4-(dimethylamino)cyclohexyl)amino)-8-ethylpyrido[3,2-d]pyrimidin-6-yl)-6-methylpyridin-2-yl)benzenesulfonamide.

22. A pharmaceutical composition comprising a of claim 1, or a pharmaceutically acceptable salt or solvate thereof, and one or more pharmaceutically acceptable excipients.

23. A method for treating or ameliorating the effects of a disease associated with altered IRE1 signaling, the method comprising administering to a subject in need thereof a compound of claim 1, or a pharmaceutically acceptable salt or solvate thereof, or a pharmaceutical composition of claim 22.

* * * * *